(12) United States Patent
Biellak et al.

(10) Patent No.: US 7,912,658 B2
(45) Date of Patent: Mar. 22, 2011

(54) SYSTEMS AND METHODS FOR DETERMINING TWO OR MORE CHARACTERISTICS OF A WAFER

(75) Inventors: Stephen Biellak, Sunnyvale, CA (US); Daniel Kavaldjiev, San Jose, CA (US)

(73) Assignee: KLA-Tencor Corp., San Jose, CA (US)

( * ) Notice: Subject to any disclaimer, the term of this patent is extended or adjusted under 35 U.S.C. 154(b) by 343 days.

(21) Appl. No.: 12/128,426

(22) Filed: May 28, 2008

(65) Prior Publication Data
US 2009/0299655 A1    Dec. 3, 2009

(51) Int. Cl.
*G06F 19/00* (2006.01)

(52) U.S. Cl. .......................... 702/40; 356/237.5

(58) Field of Classification Search .................. 702/40; 356/237.5; 250/574
See application file for complete search history.

(56) References Cited

U.S. PATENT DOCUMENTS

| | | | |
|---|---|---|---|
| 4,162,126 A | 7/1979 | Nakagawa et al. | |
| 4,410,278 A | 10/1983 | Makihira et al. | |
| 4,845,558 A | 7/1989 | Tsai et al. | |
| 4,898,471 A | 2/1990 | Vaught et al. | |
| 5,355,212 A | 10/1994 | Wells et al. | |
| 5,555,315 A | 9/1996 | Itakura | |
| 5,608,453 A | 3/1997 | Gerber et al. | |
| 5,625,451 A | 4/1997 | Schiff et al. | |
| 5,661,408 A | 8/1997 | Kamieniecki et al. | |
| 5,712,701 A * | 1/1998 | Clementi et al. ........... | 356/237.2 |
| 5,903,342 A | 5/1999 | Yatsugake et al. | |
| 5,909,276 A | 6/1999 | Kinney et al. | |
| 5,991,699 A | 11/1999 | Kulkarni et al. | |
| 6,118,525 A * | 9/2000 | Fossey et al. ............. | 356/237.2 |
| 6,171,975 B1 | 1/2001 | Hase et al. | |
| 6,201,601 B1 | 3/2001 | Vaez-Iravani et al. | |
| 6,265,719 B1 | 7/2001 | Yamazaki et al. | |
| 6,271,916 B1 | 8/2001 | Marxer et al. | |
| 6,538,730 B2 | 3/2003 | Vaez-Iravani et al. | |
| 6,552,337 B1 | 4/2003 | Cho et al. | |
| 6,558,853 B1 | 5/2003 | Kawamura | |
| 6,563,577 B2 | 5/2003 | Oomori et al. | |
| 6,596,553 B1 | 7/2003 | Lin et al. | |
| 6,603,877 B1 | 8/2003 | Bishop et al. | |
| 6,636,031 B1 | 10/2003 | Kenmochi et al. | |
| 6,718,526 B1 | 4/2004 | Eldredge et al. | |
| 6,781,688 B2 | 8/2004 | Kren et al. | |
| 6,794,885 B1 | 9/2004 | Yasumoto | |
| 6,858,859 B2 | 2/2005 | Kusunose | |
| 6,893,786 B2 | 5/2005 | Baggenstoss | |

(Continued)

FOREIGN PATENT DOCUMENTS

JP    2000-002514    1/2000
(Continued)

OTHER PUBLICATIONS

Written Opinion and International Report for PCT/US2009/045124, mailed Jan. 7, 2010.

(Continued)

*Primary Examiner* — Bryan Bui
(74) *Attorney, Agent, or Firm* — Ann Marie Mewherter

(57) ABSTRACT

Systems and methods for determining two or more characteristics of a wafer are provided. The two or more characteristics include a characteristic of the wafer that is spatially localized in at least one dimension and a characteristic of the wafer that is not spatially localized in two dimensions.

25 Claims, 3 Drawing Sheets

U.S. PATENT DOCUMENTS

| | | |
|---|---|---|
| 6,898,305 B2 | 5/2005 | Hiroi et al. |
| 6,917,419 B2 | 7/2005 | Fielden et al. |
| 6,917,433 B2 | 7/2005 | Levy et al. |
| 6,919,957 B2 | 7/2005 | Nikoonahad et al. |
| 7,006,886 B1 | 2/2006 | Huet et al. |
| 7,038,773 B2 | 5/2006 | Kuhlmann et al. |
| 7,067,819 B2 | 6/2006 | Janik |
| 7,286,218 B2 | 10/2007 | Tiemeyer et al. |
| 7,315,642 B2 | 1/2008 | Bartov et al. |
| 7,349,079 B2 | 3/2008 | Zhao et al. |
| 7,359,052 B2 | 4/2008 | Fielden et al. |
| 7,369,233 B2 | 5/2008 | Nikoonahad et al. |
| 7,373,277 B1 | 5/2008 | Wu et al. |
| 7,417,722 B2 | 8/2008 | Bills et al. |
| 7,528,944 B2 | 5/2009 | Chen et al. |
| 7,751,046 B2 | 7/2010 | Levy et al. |
| 2002/0182760 A1 | 12/2002 | Wack et al. |
| 2003/0011786 A1 | 1/2003 | Levy et al. |
| 2003/0107736 A1 | 6/2003 | Fujimoto |
| 2003/0210393 A1 | 11/2003 | Vaez-Iravani et al. |
| 2003/0228050 A1 | 12/2003 | Geshel et al. |
| 2004/0066962 A1 | 4/2004 | Sasa et al. |
| 2004/0095575 A1 | 5/2004 | Woo et al. |
| 2004/0252879 A1 | 12/2004 | Tiemeyer et al. |
| 2005/0094864 A1 | 5/2005 | Xu et al. |
| 2005/0179910 A1 | 8/2005 | Bartov |
| 2005/0186670 A1 | 8/2005 | Oh |
| 2005/0252752 A1 | 11/2005 | Fielden et al. |
| 2006/0062445 A1 | 3/2006 | Verma et al. |
| 2006/0091332 A1 | 5/2006 | Nishiyama et al. |
| 2006/0181700 A1 | 8/2006 | Andrews et al. |
| 2006/0192948 A1 | 8/2006 | Judell et al. |
| 2006/0192949 A1 | 8/2006 | Bills et al. |
| 2006/0192950 A1 | 8/2006 | Judell et al. |
| 2006/0256326 A1 | 11/2006 | Bills et al. |
| 2006/0290923 A1 | 12/2006 | Nakano et al. |
| 2007/0024998 A1 | 2/2007 | Bills et al. |
| 2007/0156379 A1 | 7/2007 | Kulkarni et al. |
| 2007/0252977 A1 | 11/2007 | Baran et al. |
| 2007/0288219 A1 | 12/2007 | Zafar et al. |
| 2008/0004823 A1 | 1/2008 | Matsushita et al. |
| 2008/0013083 A1 | 1/2008 | Kirk et al. |
| 2008/0018887 A1 | 1/2008 | Chen et al. |
| 2008/0129988 A1 | 6/2008 | Saito et al. |
| 2008/0205745 A1 | 8/2008 | Chen et al. |
| 2008/0219545 A1 | 9/2008 | Chen et al. |
| 2009/0037134 A1 | 2/2009 | Kulkarni et al. |

FOREIGN PATENT DOCUMENTS

| | | |
|---|---|---|
| JP | 2002-257518 | 9/2002 |
| JP | 2008-096430 | 4/2008 |
| KR | 10-1999-0073971 | 10/1999 |
| KR | 10-2001-0001224 | 1/2001 |
| KR | 10-0738809 | 7/2007 |
| WO | WO 2006/066135 | 6/2006 |
| WO | WO 2006/066136 | 6/2006 |
| WO | WO 2006/066137 | 6/2006 |
| WO | WO 2006/066138 | 6/2006 |
| WO | WO 2006/066139 | 6/2006 |
| WO | WO 2006/066205 | 6/2006 |
| WO | WO 2006/066206 | 6/2006 |
| WO | WO 2006/066207 | 6/2006 |
| WO | WO 2006/066255 | 6/2006 |

OTHER PUBLICATIONS

Chen et al. "Laser Scattering Correlation with Polysilicon Surface Roughness and Impact on Electical Performance," ISSM 2006.
Elson et al. "Relationship of the total integrated scattering from multilayer-coated optics to angle of incidence, polarization, correlation length, and roughness cross-correlation properties," J.M. et al, Applied Optics, 22, 3207 (1983).
Griffith, J.E. et al.; "Characterization of Scanning Probe Tips for Linewidth Measurement," J. Vac. Sci. Technol. B 9(6), Nov./Dec. 1991, pp. 3586-3589.
Holsteynes et al. "The use of unpatterned wafer inspection for immersion lithography defectivity studies." Apr. 2006.
International Search Report and Written Opinion for PCT/US08/71587 mailed on Dec. 17, 2008.
International Search Report and Written Opinion for PCT/US08/75867 mailed on Feb. 17, 2008.
International Application No. PCT/US05/45781 filed on Dec. 12, 2005.
International Search Report and Written Opinion for PCT/US07/69465 mailed on Sep. 17, 2008.
International Search Report for PCT/US07/61912 mailed Feb. 25, 2008.
Larson, C. Thomas; "Measuring Haze on Deposited Metals with Light-Scattering-Based Inspection Systems," MICRO (Sep. 1996), pp. 31-38.
Malik, Igor J. et al. "Surface Roughness of Si Wafers: Correlating AFM and Haze Measurements," Semiconductor Silicon/1994: Seventh International Symposium on Silicon Materials Science and Technology, ed. H.R. Huff, W. Bergholz and K. Sumino, The Electroche.
Marx, Egon et al. "Power spectral densities: A multiple technique study of different Si wafer surfaces," J. Vac. Sci. Technol. B 20(1), Jan./Feb. 2002, pp. 31-41.
McMillan, Wayne; "Surfscan SP2: Enabling Cost-Effective Production and the 65nm Node and Beyond," Yield Management Solutions, Summer 2004, pp. 14-23.
Nemoto et al. "Impact of Silicon Surface Roughness on Device Performance and Novel Roughness Measurement Method," IEEE/SEMI Advanced Semiconductor Manufacturing Conference, 2007.
Scheer, B.W. "Development of a physical haze and microroughness standard," SPIE vol. 2862, pp. 78-95 (1996).
Stover, John C. Optical Scattering: Measurement and Analysis, SPIE Optical Engineering Press, Bellingham, WA (1995).
U.S. Appl. No. 11/855,573 (Wu et al.) entitled Computer-Implemented Methods, Carrier Media, and Systems for Storing Image Data for a Wafer filed Sep. 14, 2007.
U.S. Appl. No. 11/855,581 (Wu et at) entitled Computer-Implemented Methods, Carrier Media, and Systems for Displaying an Image of At Least A Portion of a Wafer filed Sep. 14, 2007.
U.S. Appl. No. 60/868,769 (Fouquet et al.) entitled Methods, Designs, Defect Review Tools, and Systems for Locating Systematic Defects in A Defect Review Process filed Dec. 6, 2006.
U.S. Appl. No. 60/870,724 (Kulkarni et al.) entitled Methods and Systems for Creating Inspection Recipes Using Design Data filed Dec. 19, 2006.
U.S. Appl. No. 60/883,617 (Park et al.) entitled Methods and Systems for Using Device Information to Perform One or More Defect-Related Functions filed Jan. 5, 2007.
Written Opinion and International Search Report for PCT/US2009/051044, mailed Mar. 3, 2010.
U.S. Appl. No. 60/974,030 (Bhaskar et al.) entitled Systems and Methods for Creating Persistent Data for a Wafer and for Using Persistent Data for Inspection-Related Functions filed Sep. 20, 2007.
U.S. Appl. No. 61/074,065 (Chen et al.) entitled Computer-Implemented Methods, Computer-Readable Media, And Systems for Determining One Of More Characteristics of A Wafer filed Jun. 19, 2008.
U.S. Appl. No. 12/179,260 (Reich et al.) entitled Computer-Implemented Methods for Inspecting And/Or Classifying A Wafer filed Jul. 24, 2008.

* cited by examiner

SYSTEMS AND METHODS FOR DETERMINING TWO OR MORE CHARACTERISTICS OF A WAFER

BACKGROUND OF THE INVENTION

1. Field of the Invention

This invention generally relates to systems and methods for determining two or more characteristics of a wafer. Certain embodiments relate to a system configured to determine a characteristic of a wafer that is spatially localized in at least one dimension and a characteristic of the wafer that is not spatially localized in two dimensions.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that generally cannot be determined using inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

There are, however, a number of disadvantages to using metrology processes and tools to measure one or more characteristics of a wafer for process monitoring and control applications. For example, most metrology tools are relatively slow, particularly compared to inspection systems. Therefore, metrology processes are often performed at one location or a limited number of locations on wafers such that metrology results may be acquired in a relatively expedient manner. However, many processes used to manufacture semiconductor devices produce wafers that have characteristic(s) that vary across the surface of the wafers. As such, using metrology measurements performed at one location or a limited number of locations on a wafer may not provide sufficient information about the characteristic(s) of the wafers such that the process can be accurately monitored and controlled. Furthermore, using metrology tools to measure characteristics across the wafer for inline monitoring and control applications is not feasible due to the time in which such measurements can be performed. In particular, metrology measurements performed by currently available metrology tools such as surface roughness, resistivity, film thickness, etc. are not suitable for high sampling of wafers for inline monitoring since the measurements will impact (e.g., increase) cycle time in production.

Attempts have been made to try to use the output generated by inspection systems to determine metrology-like characteristics of wafers. For example, typically, inspection systems are configured with a number of collectors or channels. Each of these collectors or channels is able to capture multiple characteristics of the inspection surface, including, but not limited to, particles and defects of varying shapes and sizes, scratches, surface roughness, film thickness, film composition, material crystallinity, surface optical constants, nano-feature characteristics, pattern linewidths, and previous process or patterning parameters. While convenient and cost-effective, detecting multiple surface characteristics with a single collector or channel can be sub-optimal. For instance, point defects can scatter substantially strongly into a dark field collector in some cases, and dynamic range limitations of hardware or software may not permit optimal detection of a different wafer characteristic with that particular collector (e.g., relatively low amplitude, relatively long spatial frequency variations of surface roughness).

Accordingly, it would be advantageous to develop methods and systems that can be used for determining two or more characteristics of a wafer, one that is spatially localized in at least one dimension and another that is not spatially localized in two dimensions.

SUMMARY OF THE INVENTION

The following description of various system, method, and computer-readable medium embodiments is not to be construed in any way as limiting the subject matter of the appended claims.

One embodiment relates to a system configured to determine two or more characteristics of a wafer. The system includes an illumination subsystem configured to direct light to the wafer. The system also includes a first detection subsystem configured to detect light scattered from the wafer and to generate output responsive to the detected scattered light. In addition, the system includes a second detection subsystem configured to detect light scattered from the wafer and to generate output responsive to the detected scattered light. The system further includes a computer subsystem configured to determine a first characteristic of the wafer using only the output generated by one of the first and second detection subsystems and to determine a second characteristic of the wafer using only the output generated by the other of the first and second detection subsystems.

The first characteristic is spatially localized in at least one dimension. In one embodiment, the first characteristic is spatially localized in at least one dimension in that a lateral scale of the first characteristic in at least one dimension is smaller than a point spread function of the system. In another embodiment, the first characteristic includes defects on a surface of the wafer, and the defects are spatially localized in one or two dimensions.

The second characteristic is not spatially localized in two dimensions. In one embodiment, the second characteristic is not spatially localized in two dimensions in that lateral scales of the second characteristic in two dimensions are larger than a point spread function of the system. In another embodiment, the first or second detection subsystem is configured such that a substantial portion of the light scattered from the wafer that is detected by the first or second detection subsystem includes light due to wafer scattering or haze. In an additional embodiment, the second characteristic includes surface roughness, film thickness, film composition, material crystallinity, surface optical constants, nano-feature characteristics, pattern linewidths, or process parameters. In a further embodiment, the second characteristic includes surface roughness variations over only a subset of all surface spatial frequency bands of the surface roughness.

In one embodiment, the first detection subsystem is optimized for detection of only one of the first and second characteristics of the wafer and is not optimized for detection of the other of the first and second characteristics of the wafer. In another embodiment, the second detection subsystem is optimized for detection of only one of the first and second characteristics of the wafer and is not optimized for detection of the other of the first and second detection characteristics of the wafer. In an additional embodiment, the first detection subsystem is optimized for detection of only one of the first and second characteristics of the wafer and is not optimized for detection of the other of the first and second characteristics of the wafer, and the second detection subsystem is optimized for detection of only the other of the first and second characteristics of the wafer and is not optimized for detection of the one of the first and second characteristics of the wafer.

In one embodiment, the first and second detection subsystems are configured to simultaneously detect the light scattered from the wafer. In another embodiment, the first detection subsystem includes a first collector configured to collect the light scattered from the wafer, and the second detection subsystem includes a second collector configured to collect the light scattered from the wafer.

In some embodiments, solid angles of the light scattered from the wafer that is collected and detected by the first and second detection subsystems are different. In an additional embodiment, a solid angle of the light scattered from the wafer that is collected and detected by the second detection subsystem is mutually exclusive from a solid angle of the light scattered from the wafer that is collected and detected by the first detection subsystem.

In one embodiment, the second detection subsystem is optimized for detection of only one of the first and second characteristics by optimization of a solid angle of the light scattered from the wafer that is collected and detected by the second detection subsystem, a polarization of the light scattered from the wafer that is collected and detected by the second detection subsystem, a wavelength of the light scattered from the wafer that is collected and detected by the second detection subsystem, a detector of the second detection subsystem, an analog gain stage of the second detection subsystem, an analog-to-digital converter of the second detection subsystem, and digital processing performed by the second detection subsystem. In another embodiment, the maximum value of the output that can be generated and processed by the second detection subsystem is matched to the maximum value of the scattered light that would be produced by the second characteristic.

In one embodiment, the second detection subsystem includes a detector configured to detect the light scattered from the wafer, and the detector is not a photomultiplier tube. In another embodiment, a resolution of the first detection subsystem is optimized for detection of only one of the first and second characteristics and is not optimized for detection of the other of the first and second characteristics, and a resolution of the second detection subsystem is optimized for detection of the other of the first and second characteristics and is not optimized for detection of the one of the first and second characteristics.

In one embodiment, the system includes a third detection subsystem configured to detect light scattered from the wafer and to generate output responsive to the detected scattered light. In one such embodiment, the computer subsystem is configured to determine a third characteristic of the wafer using only the output generated by the third detection subsystem, and the third characteristic is not spatially localized in two dimensions.

In one embodiment, the computer subsystem is configured to determine one or more properties of a film formed on the wafer using the output generated by the first or second detection subsystem in combination with the output generated by the third detection subsystem.

In one embodiment, the illumination subsystem is configured to direct the light to the wafer at multiple angles of incidence. In one such embodiment, the first or second detection subsystem is configured to detect the light scattered from the wafer due to illumination at only a first of the multiple angles of incidence, and the third detection subsystem is configured to detect the light scattered from the wafer due to illumination at only a second of the multiple angles of incidence. In another embodiment the light directed to the wafer has multiple wavelengths. In one such embodiment, the first or second detection subsystem is configured to detect the light scattered from the wafer due to illumination with only a first of the multiple wavelengths, and the third detection subsystem is configured to detect the tight scattered from the wafer due to illumination with only a second of the multiple wavelengths.

In an additional embodiment, the second characteristic includes surface roughness variations over one or more first surface spatial frequency bands of the surface roughness, and the third characteristic includes surface roughness variations over one or more second surface spatial frequency bands of the surface roughness.

Each of the embodiments of the system described above may be further configured as described herein.

Another embodiment relates to a method for determining two or more characteristics of a wafer. The method includes directing light to the wafer using an illumination subsystem. The method also includes detecting light scattered from the wafer and generating output responsive to the detected scattered light using a first detection subsystem of a system. The method also includes detecting light scattered from the wafer and generating output responsive to the detected scattered light using a second detection subsystem of the system.

The method further includes determining a first characteristic of the wafer using only the output generated by one of the first and second detection subsystems. The first characteristic is spatially localized in at least one dimension. In addition, the method includes determining a second characteristic of the wafer using only the output generated by the other of the first and second detection subsystems. The second characteristic is not spatially localized in two dimensions.

Each of the steps of each of the embodiments of the method described above may be further performed as described herein. In addition, each of the embodiments of the method described above may include any other step(s) of any other method(s) described herein. Furthermore, each of the embodiments of the method described above may be performed by any of the systems described herein.

An additional embodiment relates to a computer-readable medium that includes program instructions executable on a computer system for performing a computer-implemented method for determining two or more characteristics of a wafer. The computer-implemented method includes determining a first characteristic of the wafer using only output generated by detecting light scattered from the wafer using one of first and second detection subsystems of a system. The first characteristic is spatially localized in at least one dimension. The computer-implemented method also includes determining a second characteristic of the wafer using only output generated by detecting light scattered from the wafer using the other of the first and second detection subsystems. The second characteristic is not spatially localized in two dimensions Each of the steps of the computer-implemented method described above may be further performed as described herein. In addition, the computer-implemented method may include any other step(s) of any other method(s) described herein. The computer-readable medium may be further configured as described herein.

BRIEF DESCRIPTION OF THE DRAWINGS

Other objects and advantages of the invention will become apparent upon reading the following detailed description and upon reference to the accompanying drawings in which.

Figure 1:
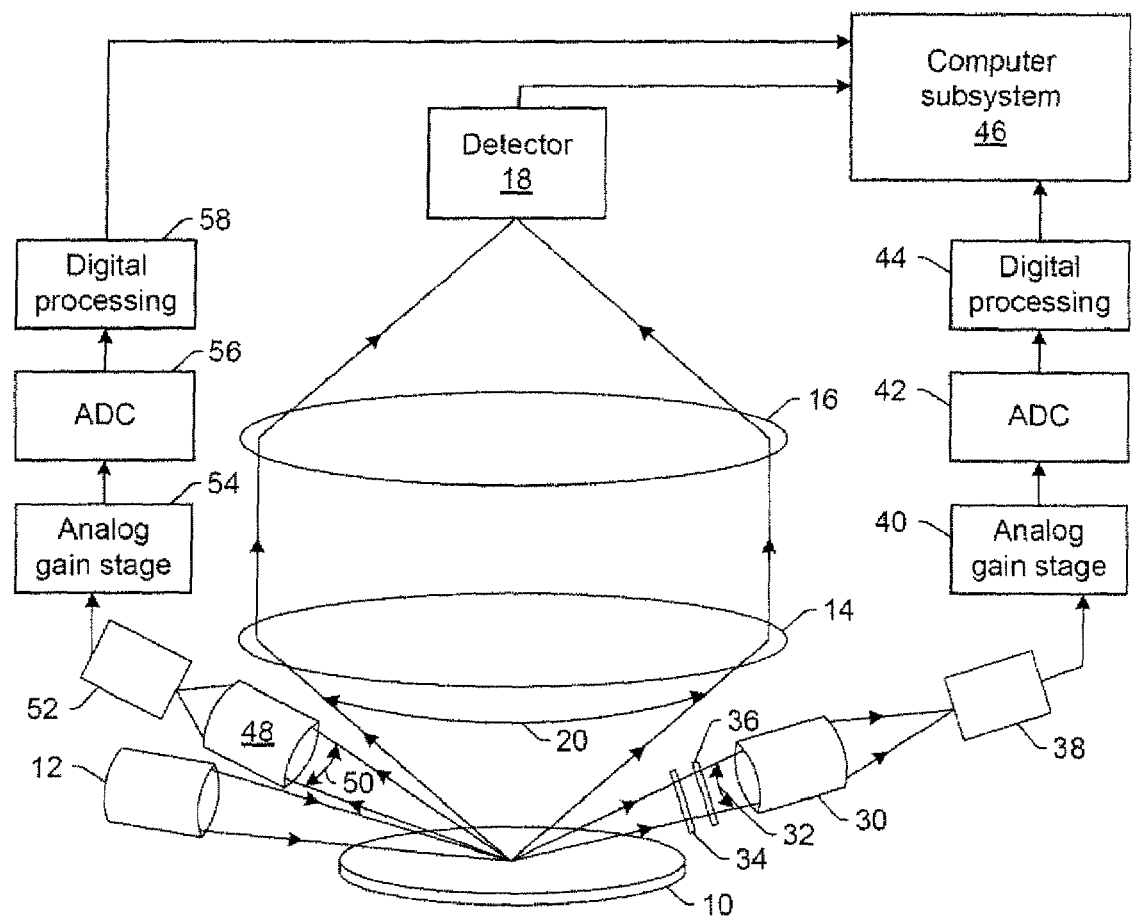
FIG. 1 is a schematic diagram illustrating a side view of one embodiment of a system configured to determine two or more characteristics of a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. In this manner, the wafer may be a patterned or an unpatterned wafer. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, the embodiments may be used for determining two or more characteristics of another specimen such as a reticle, which may also be commonly referred to as a mask or a photomask. Many different types of reticles are known in the art, and the terms "retile," "mask," and "photomask" as used herein are intended to encompass all types of reticles known in the art.

The terms "first," "second," and "third" are used herein to differentiate between to different detection subsystems, different characteristics, etc. The terms "first," "second," and "third" are not used to indicate temporal, spatial, or preferential characteristics of the detection subsystems, characteristics, etc.

Turing now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1 illustrates one embodiment of a system configured to determine two or more characteristics of a wafer. The system includes an illumination subsystem configured to direct light to wafer 10. For example, the illumination subsystem includes light source 12. Light source 12 may include any suitable light source such as a laser, a cw laser, or a pulsed laser. Light source 12 may be configured to generate light at any suitable wavelength(s) (e.g., about 355 nm or about 266 nm). In one embodiment, the light directed to the wafer has multiple wavelengths. The multiple wavelengths of light may include multiple, discrete wavelengths of light (e.g., from a polychromatic light source) or a continuous spectrum of wavelengths of light (e.g., from a broadband light source). The multiple wavelengths of light may be directed to the wafer at substantially the same time. Not all of the wavelengths of light generated by the light source may be directed to the wafer (e.g., by use of one or more filters positioned in the path of the light from the light source).

The illumination subsystem may be configured to direct the light from light source 12 to wafer 10 at an oblique angle of incidence as shown in FIG. 1. The illumination subsystem may be configured to direct the light to the wafer at any suitable oblique angle of incidence. The illumination subsystem may be further configured as described and shown herein. For example, in one embodiment, the illumination subsystem is configured to direct the light to the wafer at multiple angles of incidence. The illumination subsystem may also include any other suitable optical elements configured to direct and/or focus the light from light source 12 to wafer 10.

The system may be configured to scan the light over the wafer in a number of different manners. For example, the system may be configured to scan the light directed to the wafer across the wafer by simultaneously rotating and translating the wafer. Alternatively, the system may be configured to scan the light directed to the wafer across the wafer in the x and y directions. In either case, the system may be configured to scan the light over the wafer by controlling the position of a stage (not shown in FIG. 1) on which the wafer is disposed. The stage may include any suitable mechanical and/or robotic assembly known in the art.

The system includes a first detection subsystem configured to detect light scattered from the wafer and to generate output responsive to the detected scattered light. For example, as shown in FIG. 1, the first detection subsystem includes collector 14 configured to collect light scattered from wafer 10. Collector 14 may include any suitable refractive optical element known in the art. In addition, collector 14 may be replaced with two or more refractive optical elements and/or one or more reflective optical elements, which may include any suitable refractive and/or reflective optical element(s) arranged in any suitable configuration. For example, such refractive optical element(s) may include, but are not limited to, a tube lens, a relay lens, a collimating lens, a focusing lens, a condenser lens, or some combination thereof.

The first detection subsystem also includes refractive optical element 16. Scattered light collected by collector 14 is directed to refractive optical element 16. Refractive optical element 16 may include any of the refractive optical elements described above and may be replaced with two or more refractive optical elements and/or one or more reflective optical elements as described above. In addition, the first detection subsystem includes detector 18. Refractive optical element 16 is configured to focus the light collected by collector 14 to detector 18. Detector 18 may include any suitable detector such as a photomultiplier tube (PMT). Detector 18 is configured to generate output responsive to the detected scattered light. The output generated by the detector may include any suitable output such as analog signals responsive to the scattered light detected by the detector.

The first detection subsystem may also include any other suitable optical elements (not shown in FIG. 1) such as those described further herein (e.g., an aperture and/or a polarizer). In addition, the first detection subsystem may include any other suitable hardware or software (not shown in FIG. 1) described herein (e.g., an analog gain stage, an analog-to-digital converter (ADC), and digital processing).

In one embodiment, the first detection subsystem is optimized for detection of only one of first and second characteristics of the wafer and is not optimized for detection of the other of the first and second characteristics of the wafer. For example, the first detection subsystem may be configured (or optimized) for detection of a first characteristic of the wafer and not configured (or optimized) for detection of a second characteristic of the wafer. In particular, collector 14 of the first detection subsystem may be placed in a location determined by the surface characteristics one is interested in measuring. More specifically, the collector of the first detection subsystem may be placed in a location in the scattering hemisphere above the wafer in which the maximum amount of light scattering due to only the one of the first and second characteristics will occur. In addition, the collector of the first detection subsystem may be placed in a location in the scattering hemisphere in which the light scattering due to only the one of the first and second characteristics is substantially larger than the light scattering due to the other of the first and second characteristics of the wafer such that the first detection subsystem is optimized for detection of only the one of the first and second characteristics and is not optimized for detection of the other of the first and second characteristics. For example, the first characteristic of the wafer may scatter strongly into one area of the scattering hemisphere, but if the second characteristic of the wafer scatters strongly into a portion of that area, the collector of the first detection subsystem may be configured to collect the light scattered into the area excluding the portion of the area in which the second characteristic strongly scatters light. One or more other characteristics of the collector (e.g., solid angle 20 of collector 14) of the first detection subsystem may also be configured to optimize detection of the scattered light due to only the one of the first and second characteristics to thereby optimize the first detection subsystem for detection of only the one of the first and second characteristics.

One or more characteristics of one or more additional optical elements of the first detection subsystem may also be determined based on the characteristics of the scattered light due to only the one of the first and second characteristics. For example, one or more characteristics of a polarizer or an aperture included in the first detection subsystem may be configured (or optimized) based on one or more characteristics of the scattered light due to only the one of the first and second characteristics of the wafer to optimize the first detection subsystem for detection of only the one of the first and second characteristics. In addition, the hardware and software of the first detection subsystem (or first "channel") may be configured (or optimized) for a subset of the characteristics (e.g., only the first characteristic) of the wafer that can be determined by the system.

The first characteristic is spatially localized in at least one dimension, and the second characteristic is not spatially localized in two dimensions. More specifically, the first characteristic is spatially localized in at least one dimension extending in a plane substantially parallel to the upper surface of the wafer, and the second characteristic is not spatially localized in two dimensions extending in a plane substantially parallel to the upper surface of the wafer. In other words, the at least one dimension and the two dimensions are defined in the x-y plane of the wafer.

Figure 2:
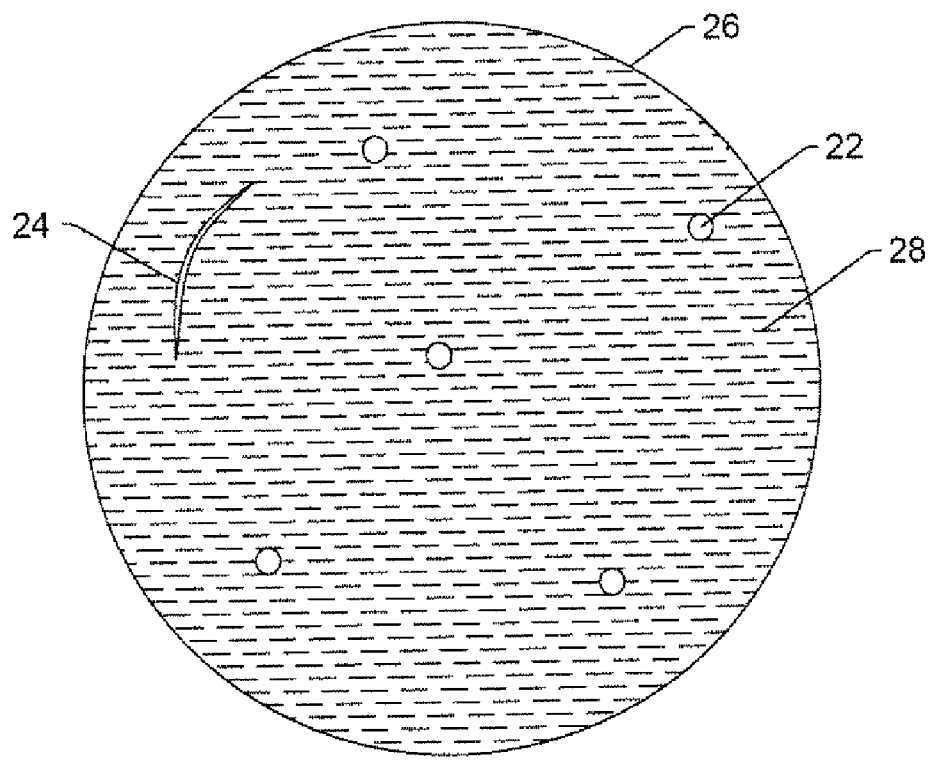
FIG. 2 is a schematic diagram illustrating a plan view of one example of a wafer having two or more characteristics, two characteristics that are spatially localized in at least one dimension and another characteristic that is not spatially localized in two dimensions.

In one embodiment, the first characteristic includes defects on a surface of the wafer, and the defects are spatially localized in one or two dimensions. For example, the first characteristic may include particles and defects of varying shapes and sizes. Examples of such particles and defects are shown in FIG. 2. In particular, particles 22 and scratch 24 are located on wafer 26. As shown in FIG. 2, particles 22 are localized in two dimensions, and scratch 24 is localized in one dimension. In other words, particles 22 have strong spatial localization in two dimensions, and scratch 24 has strong spatial localization in one dimension. In this manner, the signals produced by such defects will have strong spatial localization in at least one dimension (e.g., a scratch can be centimeters long but is usually much less than one micron wide). In another embodiment, the first characteristic is spatially localized in at least one dimension in that a lateral scale of the first characteristic in at least one dimension is smaller than a point spread function of the system. For example, the first characteristic may be defects such as point defects that are smaller than the point spread function. In this manner, "spatial localization" means on the order of the system optical point spread function or smaller. As such, the system embodiments described herein may be considered "inspection systems" in that at least one characteristic that can be determined using the systems includes "defects" that are commonly detected using inspection systems.

In an additional embodiment, the second characteristic is not spatially localized in two dimensions in that lateral scales of the second characteristic in two dimensions are larger than a point spread function of the system. For example, the second characteristic may be a wafer characteristic that can be measured on a length scale much larger than the system point spread function. In one such example, as shown in FIG. 2, the wafer may have surface roughness 28. As shown in FIG. 2, the surface roughness is not spatially localized in two dimensions in that the surface roughness extends across substantially the entire surface of wafer 26. Although a second characteristic that is not spatially localized in two dimensions may extend across substantially the entire wafer, the second characteristic may not extend across substantially the entire wafer and may still be not spatially localized in two dimensions (e.g., due to the lateral scale of the second characteristic with respect to the point spread function of the system or the length scale on which the second characteristic can be measured).

In a further embodiment, the second characteristic includes surface roughness, film thickness, film composition, material crystallinity, surface optical constants, nano-feature characteristics (e.g., nanodot parameters), pattern linewidths, or process parameters (e.g., previous process or patterning parameters). In one such embodiment, the second characteristic includes relatively low amplitude, relatively long spatial frequency variations of surface roughness. Although the first detection subsystem may not be optimized to sample such characteristics, the systems described herein are configured to sample at least one characteristic that does not have strong spatial localization in two dimensions (e.g., surface roughness or the optical constants or thickness of a deposited film and other examples described above). For example, at least one detection subsystem included in the system (e.g., the second detection subsystem described further herein) may be configured for detection of characteristic(s) with scales of tens of microns to mm to cm rather than what is typically known as "defects." In addition, although values of such second characteristics may render the wafer "defective," the characteristics themselves are generally not considered "defects" as that term is commonly used. Instead, such second characteristics are generally considered metrology-like characteristics of the wafer, which can generally not be determined using an inspection system.

In a dark field (DF) inspection system utilizing oblique incidence of the inspection beam, one may be interested in detecting and sizing particles from 30 nanometers to 1 micrometer in diameter, as well as measuring surface roughness variations over three or more surface spatial frequency bands. In this manner, the first characteristic may include the presence, size, and density of particles having diameters of 30 nanometers to 1 micrometer on the wafer, and the second characteristic may include surface roughness variations over three or more surface spatial frequency bands. For such a first characteristic, the first detection subsystem may include a collector configured to capture a relatively large solid angle (e.g., solid angle 20 shown in FIG. 1) of the scattering hemisphere, which would be advantageous for detecting such particles. However, a relatively large solid angle of collection captures a relatively large range of surface roughness spatial frequencies, averaging over all of them. Therefore, in cases in which the spatial frequency distribution of surface roughness is of interest, this collector may not be optimal. In this manner, the first detection subsystem may include a collector configured to capture a relatively large solid angle of the scattering hemisphere such that the first detection subsystem is configured (or optimized) for detection of the first characteristic and is not configured (or optimized) for detection of the second characteristic.

The system includes a second detection subsystem configured to detect light scattered from the wafer and to generate output responsive to the detected scattered light. In one embodiment, the second detection subsystem is optimized for detection of only one of the first and second characteristics of the wafer and is not optimized for detection of the other of the first and second characteristics of the wafer. For example, the second detection subsystem may be optimized for detection of the second characteristic and not optimized for detection of the first characteristic. In addition, the first and second detection subsystems may be configured (or optimized) for detection of different characteristics of the wafer. For example, in one embodiment, the first detection subsystem is optimized for detection of only one of the first and second characteristics of the wafer and is not optimized for detection of the other of the first and second characteristics of the wafer, and the second detection subsystem is optimized for detection of only the other of the first and second characteristics of the wafer and is not optimized for detection of the one of the first and second characteristics of the wafer.

As shown in FIG. 1, the second detection subsystem includes collector 30 configured to collect light scattered from wafer 10. Collector 30 may include any suitable refractive optical element. In addition, collector 30 may be replaced with two or more refractive optical elements and/or one or more reflective optical elements, which may include any suitable refractive and/or reflective optical element(s) arranged in any suitable configuration. For example, such refractive optical element(s) may include, but are not limited to, a tube lens, a relay lens, a collimating lens, a focusing lens, a condenser lens, or some combination thereof.

One or more characteristics of collector 30 such as solid angle 32 across which the collector collects light scattered from the wafer and the position of the collector within the scattering hemisphere may be determined as described further herein such that the second detection subsystem is configured (or optimized) for detection of one of the first and second characteristics (e.g., the second characteristic). Although the collector of the second detection subsystem is shown in FIG. 1 as collecting light across a particular solid angle (solid angle 32) of the scattering hemisphere, the solid angle across which the collector of the second detection subsystem is configured to collect the light scattered from the wafer may vary from that shown in FIG. 1 depending on, for example, a characteristic of the wafer for which the second detection subsystem is configured (or optimized) and a characteristic of the wafer for which the second detection subsystem is not configured (or optimized).

In some embodiments, the second detection subsystem includes polarizer 34 and aperture 36 positioned in the path of the light scattered from the wafer that is collected by collector 30. Polarizer 34 may include any suitable polarizer, and one or more characteristics of polarizer 34 may be determined as described further herein to configure (or optimize) the second detection subsystem for detection of one of the first and second characteristics (e.g., the second characteristic). Aperture 36 may include any suitable aperture, and one or more characteristics of aperture 36 may be determined as described further herein to configure (or optimize) the second detection subsystem for detection of one of the first and second characteristics (e.g., the second characteristic).

The second detection subsystem also includes detector 38. Detector 38 is configured to detect the scattered light collected by collector 30 and to generate output responsive to the detected scattered light. The output generated by detector 38 may include analog signals responsive to the detected scattered light. Detector 38 may include any suitable detector, and one or more characteristics of detector 38 may be determined as described farther herein to configure (or optimize) the second detection subsystem for detection of one of the first and second characteristics (e.g., the second characteristic).

The second detection subsystem also includes analog gain stage 40. Analog gain stage 40 may include any suitable analog gain stage and is configured to apply a gain to the output generated by detector 38. One or more characteristics of analog gain stage 40 may be determined as described further herein to configure (or optimize) the second detection subsystem for detection of one of the first and second characteristics (e.g., the second characteristic). The second detection subsystem also includes ADC 42. ADC 42 may include any suitable ADC and is configured to covert analog signals generated by analog gain stage 40 to digital signals. One or more characteristics of ADC 42 may be determined as described further herein to configure (or optimize) the second detection subsystem for detection of one of the first and second characteristics (e.g., the second characteristic). The second detection subsystem further includes digital processing 44. Digital processing 44 may include any suitable hardware or software and may be configured to process the digital signals produced by ADC 42 in any suitable manner or manners. One or more characteristics of digital processing 44 may be determined as described further herein to configure (or optimize) the second detection subsystem for detection of one of the first and second characteristics (e.g., the second characteristic).

As noted above, the second detection subsystem may be optimized for detection of only one of the first and second characteristics (e.g., the second characteristic) and not optimized for detection of the other of the first and second characteristics (e.g., the first characteristic). For example, collector 30 of the second detection subsystem may be placed in a location determined by only one of the surface characteristics one is interested in measuring. More specifically, the collector of the second detection subsystem may be placed in a location in the scattering hemisphere in which the maximum amount of light scattering due to only one of the characteristics will occur. In addition, the collector of the second detection subsystem may be placed in a location in the scattering hemisphere in which the light scattering due to only one of the characteristics is substantially larger than the light scattering due to the other characteristic such that the second detection subsystem is optimized for detection of only the one characteristic and is not optimized for detection of the other characteristic. For example, one of the characteristics of the wafer may scatter strongly into one area of the scattering hemisphere, but if the other characteristic of the wafer also scatters strongly into a portion of that area the collector of the second detection subsystem may be configured to collect the light scattered into the area except the portion of the area in which the other characteristic strongly scatters light.

In one embodiment, the first or second detection subsystem is configured such that a substantial portion of the light scattered from the wafer that is detected by the first or second detection subsystem includes light due to wafer scattering or haze. For example, the second detection subsystem may be configured such that a substantial portion of the light scattered from the wafer that is detected by the second detection subsystem includes light due to wafer scattering or haze.

Typically, good point defect detectors are designed to minimize the amount of haze or surface scatter collected. However, in embodiments described herein, one or more additional collectors (e.g., collector 30) can be placed in locations where the haze is larger (i.e., locations in which the amount of the light scattered due to the haze is larger in the scattering hemisphere). In addition, the one or more additional collectors can be placed in locations where the scattering from spatially localized characteristics (e.g., defects) of the wafer is smaller. As such a substantial portion of the light collected and detected by one of the detection subsystems (e.g., the second detection subsystem) may include light due to wafer scattering or haze instead of scattering due to spatially localized characteristics. In addition to the second characteristics described herein, there are many other sample characteristics that can be determined through analysis of the wafer surface scattering or haze.

Although the collector of the first or second detection subsystem may be positioned as described above to maximize the amount of light scattering due to the wafer surface or haze that is detected by the first or second detection subsystem, the first or second detection subsystem may be configured in other manners to maximize the amount of light scattering due to the wafer surface or haze detected. For example, the collector of the first or second detection subsystem may be configured such that the collection space of the collector includes areas in which the light scattering due to the haze is maximized and areas in which the light scattering due to the haze is lower. In such an example, the second detection subsystem may include one or more optical elements such as aperture 36, which may be configured to control which portion of the scattered light is collected by the collector. In particular, aperture 36 may be positioned between the wafer and the collector and configured to block light scattered in the collection space of the collector except in areas in which the light scattered due to the haze is maximized. In such embodiments, the detector may be an array detector (e.g., a two-dimensional array detector) configured to detect light across the entire collection space of the collector. Alternatively, the position of the detector may be altered depending on the location of the maximum scattered light due to haze within the collection space of the collector.

One or more other characteristics of the collector (e.g., solid angle 32 of collector 30) of the second detection subsystem may also be selected to configure (or optimize) the detection of the scattered light due to only one of the first and second characteristics (e.g., the second characteristic) to thereby configure (or optimize) the second detection subsystem for detection of only the one of the first and second characteristics (e.g., the second characteristic). For example, in one embodiment, solid angles of the light scattered from the wafer that is collected and detected by the first and second detection subsystems are different. In one such example, a solid angle of the light scattered from the wafer that is collected and detected by the second detection subsystem may be smaller than a solid angle of the light scattered from the wafer that is collected and detected by the first detection subsystem. In particular, as noted above, the first detection subsystem may include collector 14 configured to capture a relatively large solid angle (e.g., solid angle 20) of the scattering hemisphere such that the first detection subsystem is configured (or optimized) for detection of only one of the characteristics (e.g.) the first characteristic) and is not optimized for detection of another of the characteristics (e.g., the second characteristic). For example, the first detection subsystem may include one relatively large solid angle, DF collector dedicated to detecting point defects. On the other hand, the second detection subsystem may include a smaller solid angle DF collector (collector 30) or channel such that the second detection subsystem is configured (or optimized) to detect and measure a surface roughness characteristic or other non-spatially localized characteristic of the wafer. For example, as noted above, the second detection subsystem may include collector 30 configured to capture a relatively small solid angle (e.g., solid angle 32) of the scattering hemisphere such that the second detection subsystem is configured (or optimized) for detection of the second characteristic and is not configured (or optimized) for detection of the first characteristic. In particular, the second detection subsystem may include one relatively small solid angle, DF collector dedicated to detecting one or more non-spatially localized characteristics of the wafer. However, in other embodiments, all (or some) of the physical collectors included in the detection subsystems may subtend the same solid angle. For example, the collectors included in the first and second detection subsystems may capture the same solid angle of the scattering hemisphere.

In one embodiment, the first detection subsystem includes a first collector configured to collect the light scattered from the wafer, and the second detection subsystem includes a second collector configured to collect the light scattered from the wafer. For example, in the embodiment shown in FIG. 1, the first detection subsystem includes collector 14, and the second detection subsystem includes collector 30. In addition, one or more characteristics of each of the collectors may be configured (or optimized) for detection of different characteristics. One or more elements of the different detection subsystems coupled to each of the collectors may also be individually configured (or optimized) for detection of the different characteristics of the wafer. Therefore, using different collectors for the different detection subsystems can make configuration (or optimization) of the system for detection of substantially different characteristics of the wafer, at least one of which is spatially localized in at least one dimension and at least one of which is not spatially localized in two dimensions, less complicated.

In one embodiment, a solid angle of the light scattered from the wafer that is collected and detected by the second detection subsystem is mutually exclusive from a solid angle of the light scattered from the wafer that is collected and detected by the first detection subsystem. The solid angles of the light scattered from the wafer that are collected and detected by the different detection subsystems may be mutually exclusive if, for example as described above, the different detection subsystems include different collectors. In addition, the solid angles of the scattered light that are collected and detected by the different detection subsystems may be mutually exclusive in that one detection subsystem may not collect and detect light across any portion of the solid angle across which the scattered light is collected and detected by another detection subsystem. In other words, the same scattered light rays may not be collected and detected by both detection subsystems. In addition, the solid angles of the scattered light that are collected and detected by the different detection subsystems may not overlap in any manner. In other words, one of the detection subsystems may not collect and detect any of the scattered light rays that are located within a solid angle of the scattered light that is collected and detected by another of the detection subsystems. Such embodiments of the system may be different than other systems in that the system embodiments may not include a single collector or channel being used as the first and second detection subsystems (e.g., via optical or other partitioning of the collection and detection space). In other words, the system embodiments described herein may not be configured to use output generated by a single collector or channel to detect at least one characteristic of the wafer that is spatially localized in at least one dimension and at least another characteristic of the wafer that is not spatially localized in two dimensions.

Such embodiments of the system are structurally different than systems that segment collection space of a single collector or detection space of a single detector such that different portions of the collection or detection space can be used to detect different characteristics. Furthermore, such embodiments of the system may be advantageous over other systems that segment collection space of a single collector or detection space of a single detector for detection of different characteristics if one or more characteristics of other elements coupled to the collector or detector such as a polarizer, an aperture, an analog gain stage, an ADC, or digital processing are not or cannot be configured (or optimized) such that the one or more characteristics of the elements can be independently configured (or optimized) for detection of each of the different characteristics of the wafer.

One or more characteristics of one or more additional optical elements of the second detection subsystem may also be selected based on the characteristics of the scattered light due to only one of the two or more characteristics (e.g., the second characteristic). For example, one or more characteristics of polarizer 34 or aperture 36 included in the second detection subsystem may be configured (or optimized) based on one or more characteristics of the scattered light due to only one of the characteristics (e.g., the second characteristic) of the wafer to configure (or optimize) the second detection subsystem for detection of only the one of the characteristics (e.g., the second characteristic). In addition, the hardware and software of the second detection subsystem (or second "channel") may be configured (or optimized) for a subset of the characteristics (e.g., only the second characteristic) of the wafer that can be determined by the system.

In one embodiment, the second detection subsystem is optimized for detection of only one of the first and second characteristics (e.g., the second characteristic) by optimization of a solid angle of the light scattered from the wafer that is collected and detected by the second detection subsystem, a polarization of the light scattered from the wafer that is collected and detected by the second detection subsystem, a wavelength of the light scattered from the wafer that is collected and detected by the second detection subsystem, a detector of the second detection subsystem, an analog gain stage of the second detection subsystem, an ADC of the second detection subsystem, and digital processing performed by the second detection subsystem. For example, in saying that the second detection subsystem (the detection subsystem that includes the smaller collector or channel) is optimized, the second detection subsystem may have a particular solid angle of collection (e.g., solid angle 32), collect and detect a specific light polarization (e.g., determined by polarizer 34), collect and detect a specific light wavelength or wavelengths (which may be determined by the wavelength(s) of light directed to the wafer and/or one or more spectral filters (not shown) included in the second detection subsystem) and have a detection element (e.g., detector 38), analog gain stage 40, ADC 42, and digital processing 44 designed for the best detection or measurement of one or more characteristics of interest.

As described above, the second detection subsystem may be configured or used for detection of the second characteristic. In one embodiment, the maximum value of the output that can be generated and processed by the second detection subsystem is matched to the maximum value of the scattered light that would be produced by the second characteristic. For example, the maximum value of the scattered light that would be produced by surface scattering or haze may be determined or estimated, and the second detection subsystem may be configured such that the maximum value of the output of the second detection subsystem matches the maximum value of the scattered light. In one such example, the detection range of the second detection subsystem may be matched to the maximum value of the scattered light produced by surface scattering or haze such that the maximum range of the scattered light can be detected with the maximum resolution. The detection range of the second detection subsystem may be matched in such a manner by selecting the dynamic range and/or gain of a detector or analog gain stage of the second detection subsystem (in addition to other characteristics of the second detection subsystem described herein such as placement of the collector, etc.) such that the detection range of the second detection subsystem corresponds to the range of scattered light produced by surface scattering or haze. In one such example, the gain of the detector of the second detection subsystem may be "matched" to the maximum scattered light due to haze that will be detected by the second detection subsystem. In this manner, a relatively small change in the second characteristic of the wafer may correspond to a relatively small change in the output of the second detection subsystem thereby allowing the second characteristic to be determined with better resolution than if output generated by detection subsystems that are not matched in such a manner were used for determination of the second characteristic.

In a similar manner, in one embodiment, a resolution of the first detection subsystem is optimized for detection of only one of the first and second characteristics and is not optimized for detection of the other of the first and second characteristics, and a resolution of the second detection subsystem is optimized for detection of the other of the first and second characteristics and is not optimized for detection of the one of the first and second characteristics. The first and second detection subsystems may be configured (or optimized) in this manner as described further herein. For instance, the first and second detection subsystems may be configured for detection of the first or second characteristic with the optimal resolution by selecting one or more characteristics of detectors, analog gain stages, ADCS, digital processing, or some combination thereof included in the first and second detection subsystems as described further herein.

As described above, the second detection subsystem may be configured or used for detection of the second characteristic. In one embodiment, the second detection subsystem includes a detector configured to detect the light scattered from the wafer, and the detector is not a PMT. For example, the detection element (e.g., detector 38) in this detection subsystem does not have to be and may preferably not be a PMT, which can be damaged by exposure to relatively large haze levels. Instead, detector 38 may be a charge coupled device (CCD) camera, a time delay integration (TDI) camera, a photodiode, or any other detector that provides adequate sensitivity to the light scattering due to the haze while decreasing the probability that the detector will be damaged due to the level of the light scattered due to the haze.

In one embodiment, the second characteristic includes surface roughness variations over only a subset of all surface spatial frequency bands of the surface roughness. For example, the second detection subsystem may be configured (or optimized) for detection of only a portion of all of the surface spatial frequency bands of the surface roughness. As such, the systems described herein may be configured to provide more detailed information about the surface roughness than systems that use a detection subsystem to determine information about the surface roughness across all surface spatial frequency bands. In particular, when a spot on a wafer having roughness is illuminated, the surface roughness acts like a light grating with the distribution of the surface roughness as a function of the spatial frequency bands. In this manner, in systems that use a detection subsystem to determine information about the surface roughness across all surface spatial frequency bands, the output generated by the detection subsystem can only be used to determine a single value for the surface roughness that is an average (or another function) of all of the surface spatial frequency bands. Therefore, such systems provide less detailed information about the surface roughness. However, by configuring (or optimizing) one of the detection subsystems (e.g., the second detection subsystem) as described herein for detection of only a portion of all of the surface spatial frequency bands of the surface roughness, more detailed information may be provided about the surface roughness.

The principles described above can be generalized to other characteristics besides surface roughness and point defects. For instance, nanodot arrays (e.g., arrays of substantially small etched holes having dimensions on the order of about 10 nm to about 20 nm and spaced apart from each other within the array by about 10 nm to about 20 nm) may have characteristics such as nanodot size, shape, and density, which are best determined by measuring relatively low frequency variations in surface scattering at various locations in the scattering hemisphere. Better resolution of these characteristics may be obtained by having separate collectors to look for them, while simultaneously being designed to be less sensitive to point defects. One way to accomplish this is configuring an optical polarizer (e.g., polarizer 34) in the nanodot characteristic collector to reduce the signal from point defects. In this manner, one of the detection subsystems (e.g., the second detection subsystem) may be configured (or optimized) to detect the second characteristic and not configured (or optimized) to detect the first characteristic.

In this manner, the system may include multiple detection subsystems, at least one of which is configured (or optimized) for detection of a characteristic of the wafer that is not spatially localized. In contrast, other inspection systems that include multiple collectors typically use the multiple collectors for the advantages of detection and differentiation of spatially localized characteristics of wafers such as specific point or extended defects including, but not limited to, particles, pits, scratches, dimples, micro-scratches, etc. However, such inspection systems do not include one or more detection subsystems configured (or optimized) for detection of one or more characteristics of the wafer that are not spatially localized in two dimensions and not configured (or optimized) for detection of one or more characteristics of the wafer that are spatially localized in at least one dimension. For example, as described further herein, the embodiments described herein may advantageously include multiple collectors/channels, at least one of which may be configured (or optimized) for measuring a sample characteristic on a length scale much larger than the system point spread function, while other collectors/channels can be configured (or optimized) for detection of characteristics such as point defects that are smaller than the point spread function.

In this manner, the system includes multiple detection subsystems, which may be individually configured (or optimized) for a surface characteristic of interest. In addition, as described further herein, each of the detection subsystems may include a collection subsystem, and the collection subsystem of each detection subsystem may be individually configured (or optimized) for a surface characteristic of interest. In this manner, the system may include multiple collection subsystem& which may be individually optimized for the surface characteristics of interest. In one embodiment, the first and second detection subsystems are configured to simultaneously detect the light scattered from the wafer. For example, as the illumination subsystem illuminates the wafer and/or scans the light across the wafer, the first and second detection subsystems may both collect and detect light scattered from the wafer. In this manner, the system utilizes multiple (greater than two) simultaneous collectors, which may be placed in locations determined by the surface characteristics one is interested in measuring and hardware and software of each collector or channel may be configured (or optimized) for only a subset of characteristics, which can improve the inspection system performance. As such in one embodiment, the system may be configured as a surface inspection apparatus configured (or optimized) for simultaneous measurement of multiple surface characteristics and defects. In particular, the system may be configured as a surface inspection system that can measure multiple surface characteristics simultaneously by utilizing multiple detection subsystems, which may be individually optimized for the surface characteristics of interest.

The system also includes a computer subsystem configured to determine a first characteristic of the wafer using only the output generated by one of the first and second detection subsystems and to determine a second characteristic of the wafer using only the output generated by the other of the first and second detection subsystems. For example, as shown in FIG. 1, the system includes computer subsystem 46. The output generated by the first detection subsystem may be provided to the computer subsystem. For example, computer subsystem 46 may be coupled to detector 18 of the first detection subsystem (e.g., via one or more transmission media, which may include any suitable transmission media known in the art). The computer subsystem may be coupled to the detector such that the computer subsystem can receive the output generated by the detector. In addition, if the first detection subsystem includes additional elements such as an analog gain stage, an ADC, and digital processing, the computer subsystem may be coupled to the digital processing hardware or software such that the computer subsystem can receive the digitally processed output generated by the detector. The computer subsystem may be configured to use the output generated by the first detection subsystem to determine any of the characteristics (e.g., a first characteristic) of the wafer described herein. The computer subsystem may be configured to use the output and any suitable algorithm and/or method to determine the characteristic (e.g., the first characteristic) of the wafer.

In a similar manner, the output generated by the second detection subsystem may be provided to the computer subsystem. For example, computer subsystem 46 may be coupled to digital processing 44 of the second detection subsystem (e.g., via one or more transmission media, which may include any suitable transmission media known in the art). The computer subsystem may be coupled to the digital processing such that the computer subsystem can receive the digitally processed output generated by the detector. The computer subsystem may be configured to use the output generated by the digital processing to determine any of the characteristics (e.g., a second characteristic) of the wafer described herein. The computer subsystem may be configured to use the output and any suitable algorithm and/or method to determine the characteristic (e.g., the second characteristic) of the wafer. In this manner, computer subsystem 46 is configured to separately process output from the different detection subsystems and to separately determine the different characteristics using the different output.

The computer subsystem may take various forms, including a personal computer system, image computer, mainframe computer system, workstation, network appliance, Internet appliance, or other device. In general, the term "computer subsystem" may be broadly defined to encompass any device having one or more processors, which executes instructions from a memory medium. The computer subsystem may also include any suitable processor known in the art such as a parallel processor. In addition, the computer subsystem may include a computer platform with high speed processing and software, either as a standalone or a networked tool.

In some embodiments, the computer subsystem may be configured to store all of the output generated by one or both of the first and second detection subsystems for the entire wafer or the entire portion of the wafer that is scanned and to determine one or more properties of the first and/or second characteristics as a function of location on the wafer using all of the stored output for the wafer. In some such embodiments, the computer subsystem may be configured to determine variations in the first and/or second characteristics over the entire wafer or the entire portion of the wafer that is scanned as a function of position across the wafer. In additional such embodiments, the computer subsystem may be configured to determine the first and/or second characteristics using all of the stored output for the wafer (e.g., an average value or some statistical value of the first and/or second characteristics across the entire wafer or the entire portion of the wafer). In such embodiments, the computer subsystem may be configured as described in commonly owned U.S. Patent Application Ser. No. 60/974,030 by Bhaskar et al. filed Sep. 20, 2007, which is incorporated by reference as if fully set forth herein. The embodiments described herein may be configured to perform any step(s) of any method(s) described in this patent application.

The computer subsystem may also use the output from one of the detection subsystems to influence the processing of the output from another of the detection subsystems. For example, the output from the second detection subsystem may influence the processing of the output from the first detection subsystem. For examples looking at the dedicated surface channel (or combination of channels), one might decide to lower or raise the threshold for the defect detection channel.

In one embodiment, the system includes a third detection subsystem configured to detect light scattered from the wafer and to generate output responsive to the detected scattered light. For example, as shown in FIG. 1, the third detection subsystem includes collector 48 configured to collect light scattered from wafer 10. Collector 48 may include any suitable refractive optical element known in the art. In addition, collector 48 may be replaced with two or more refractive optical elements and/or one or more reflective optical elements, which may include any suitable refractive and/or reflective optical element(s) arranged in any suitable configuration. For example, such refractive optical element(s) may include, but are not limited to, a tube lens, a relay lens, a collimating lens, a focusing lens, a condenser lens, or some combination thereof. One or more characteristics of collector 48 such as solid angle 50 across which the collector collects light scattered from the wafer and the position of the collector within the scattering hemisphere may be determined as described further herein to configure (or optimize) the third detection subsystem for detection of a third or other characteristic of the wafer. Although the collector of the third detection subsystem is shown in FIG. 1 as collecting light across a particular solid angle (solid angle 50) of the scattering hemisphere, the solid angle across which the collector of the third detection subsystem is configured to collect the light scattered from the wafer may vary from that shown in FIG. 1 depending on, for example, the third or other characteristic of the wafer that is being detected by the third detection subsystem.

The third detection subsystem may include a polarizer (not shown in FIG. 1) and an aperture (not shown in FIG. 1) positioned in the path of the scattered light collected by collector 48. The polarizer may include any suitable polarizer, and one or more characteristics of the polarizer may be determined as described further herein to configure (or optimize) the third detection subsystem for detection of the third or other characteristic. The aperture may include any suitable aperture, and one or more characteristics of the aperture may be determined as described further herein to configure (or optimize) the third detection subsystem for detection of the third or other characteristic.

The third detection subsystem also includes detector 52. Detector 52 is configured to detect the scattered light collected by collector 48 and to generate output responsive to the detected scattered light. The output generated by detector 52 may include signals responsive to the detected scattered light. Detector 52 may include any suitable detector, and one or more characteristics of detector 52 may be determined as described further herein to configure (or optimize) the third detection subsystem for detection of the third or other characteristic.

The third detection subsystem also includes analog gain stage 54. Analog gain stage 54 may include any suitable analog gain stage and is configured to apply a gain to the output generated by detector 52. One or more characteristics of analog gain stage 54 may be determined as described further herein to configure (or optimize) the third detection subsystem for detection of the third or other characteristic. The third detection subsystem also includes ADC 56. ADC 56 may include any suitable ADC and is configured to covert the analog signal generated by analog gain stage 54 to a digital signal. One or more characteristics of ADC 56 may be determined as described further herein to configure (or optimize) the third detection subsystem for detection of the third or other characteristic. The third detection subsystem further includes digital processing 58. Digital processing 58 may include any suitable hardware or software and may be configured to process the digital signal produced by ADC 56 in any suitable manner or manners. One or more characteristics of digital processing 58 may be determined as described further herein to configure (or optimize) the third detection subsystem for detection of the third or other characteristic.

The third detection subsystem may be configured (or optimized) for detection of the third characteristic of the wafer and not configured (or optimized) for detection of the first and second characteristics. The third characteristic may not be spatially localized in two dimensions. The third characteristic of the wafer may include any of such characteristics described herein (e.g., any characteristics described herein that are not spatially localized in two dimensions). The third detection subsystem may be configured (or optimized) for detection of such a third characteristic as described further herein and may not be configured (or optimized) for detection of the first and second characteristics as described further herein. For example, collector 48 of the third detection subsystem may be placed in a location determined by the surface characteristics one is interested in measuring. More specifically, the collector of the third detection subsystem may be placed in a location in the scattering hemisphere in which the maximum amount of light scattering due to the third characteristic will occur. In addition, the collector of the third detection subsystem may be placed in a location in the scattering hemisphere in which the light scattering due to the third characteristic is substantially larger than the light scattering due to the first and second characteristics such that the third detection subsystem is configured (or optimized) for detection of the third characteristic and is not configured (or optimized) for detection of the first and second characteristics.

One or more other characteristics (e.g., solid angle 50) of the collector of the third detection subsystem may also be selected to configure (or optimize) the detection of the scattered light due to the third characteristic to thereby configure (or optimize) the third detection subsystem for detection of the third characteristic. One or more characteristics of one or more additional optical elements of the third detection subsystem may also be selected based on the characteristics of the scattered light due to the third characteristic. For example, one or more characteristics of a polarizer or an aperture included in the third detection subsystem may be configured (or optimized) based on one or more characteristics of the scattered light due to the third characteristic of the wafer to configure (or optimize) the third detection subsystem for detection of the third characteristic. In addition, the hardware and software of the third detection subsystem (or third "channel") may be configured (or optimized) for a subset of the characteristics (e.g., only the third characteristic) of the wafer that can be determined by the system.

A solid angle of the light scattered from the wafer that is collected and detected by the third detection subsystem may be smaller than the solid angle of the light scattered from the wafer that is collected and detected by the first detection subsystem. For example, as noted above, the first detection subsystem may include collector 14 configured to capture a relatively large solid angle (e.g., solid angle 20) of the scattering hemisphere such that the first detection subsystem may be configured (or optimized) for detection of the first characteristic and may not be configured (or optimized) for detection of the second and third characteristics. In this manner the first detection subsystem may include one relatively large solid angle DF collector dedicated to detecting point defects such that the first detection subsystem is optimized for detection of the first characteristic and is not optimized for detection of the second or third characteristic. In particular, the first detection subsystem may include one relatively large solid angle, DF collector dedicated to detecting point defects. On the other hand, the third detection subsystem may include a smaller solid angle DF collector (collector 48) or channel such that the third detection subsystem may be configured (or optimized) to detect and measure a surface roughness characteristic of the wafer. For example, as noted above, the third detection subsystem includes collector 48, which may be configured to capture a relatively small solid angle (e.g., solid angle 50) of the scattering hemisphere such that the third detection subsystem may be configured (or optimized) for detection of the third characteristic and may not be configured (or optimized) for detection of the first and second characteristics. In particular, the third detection subsystem may include one relatively small solid angle, DF collector dedicated to detecting a non-spatially localized characteristic of the wafer. In this manner, the second and third detection subsystems may include two smaller solid angle DF collectors or channels, each configured (or optimized) to detect and measure a different surface roughness characteristic of the wafer, which may be advantageous as described further herein.

However, all (or some) of the physical collectors included in the detection subsystems may subtend the same solid angle. For example, the collectors included in the second and third detection subsystems may capture the same solid angle of the scattering hemisphere, and the first detection subsystem may capture a different solid angle of the scattering hemisphere. In another example, the collectors included in the first and third detection subsystems may capture the same solid angle of the scattering hemisphere, and the second detection subsystem may capture a different solid angle of the scattering hemisphere. In an additional example, the collectors included in the first, second, and third detection subsystems may capture the same or different solid angles of the scattering hemisphere.

The third detection subsystem may be further configured (or optimized) for detection of the third characteristic and further not configured (or optimized) for detection of the first and second characteristics as described further herein.

In one embodiment, the computer subsystem is configured to determine a third characteristic of the wafer using only the output generated by the third detection subsystem, and the third characteristic is not spatially localized in two dimensions. For example, computer subsystem 46 may be coupled to the third detection subsystem as described further herein such that the computer subsystem can receive the output generated by the third detection subsystem. In addition, the computer subsystem may be configured to determine the third characteristic using only the output generated by the third detection subsystem as described further herein. The computer subsystem may be configured to use the output generated by the third detection subsystem and any suitable algorithm and/or method to determine the third characteristic of the wafer.

In one embodiment, the computer subsystem is configured to determine one or more properties of a film formed on the wafer using the output generated by the first or second detection subsystem in combination with the output generated by the third detection subsystem. For example, the computer subsystem may be configured to use the haze signal from multiple detection subsystems (e.g., two or more of the multiple detection subsystems, which may be configured (or optimized) for detection of characteristics that are not spatially localized in two dimensions) to determine the properties of a deposited film. In one such example, the surface roughness of a deposited film may be coupled to the film thickness in that the surface roughness and the film thickness are not independent of each other. Therefore, unless one is inspecting a surface without a film, the surface roughness and film thickness of the surface generally cannot be determined with just one measurement. Instead, in embodiments described herein, the measurements performed by two or more detection subsystems (e.g., the first or second detection subsystem and the third detection subsystem), each of which may be configured (or optimized) for detection of a characteristic that is not spatially localized in two dimensions, may be used in combination by the computer subsystem to determine the surface roughness and the film thickness more accurately. The computer subsystem may use the output generated by the first or second detection subsystem and the third detection subsystem and any suitable method or algorithm to determine the one or more properties of the film.

In one embodiment, the second characteristic includes surface roughness variations over one or more first surface spatial frequency bands of the surface roughness, and the third characteristic includes surface roughness variations over one or more second surface spatial frequency bands of the surface roughness. For example, the second and third detection subsystems may be configured (or optimized) for detection of different surface spatial frequency bands of the surface roughness. As such, the systems described herein may be configured to provide more detailed information about the surface roughness than systems that use a single detection subsystem to determine information about the surface roughness. In particular, when a spot on a wafer having roughness is illuminated, the surface roughness acts like a light grating with the distribution of the surface roughness as a function of the spatial frequency bands. In this manner, in systems that use a single detection subsystem to determine information about the surface roughness, the single detection subsystem is generally configured to detect scattered light due to all surface spatial frequency bands of the surface roughness thereby providing a single value for the surface roughness that is an average (or another function) of all of the surface spatial frequency bands. Therefore, such systems provide less detailed information about the surface roughness. However, by configuring (or optimizing) two or more of the detection subsystems as described herein for detection of only a portion of all of the surface spatial frequency bands of the surface roughness, more detailed information may be provided about the surface roughness.

Figure 3:
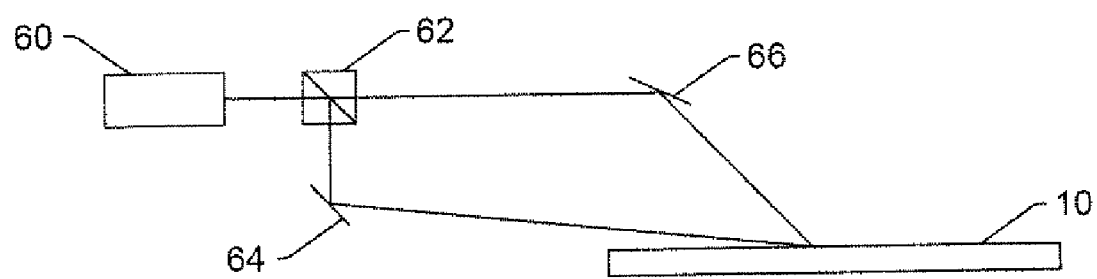
FIG. 3 is a schematic diagram illustrating a side view of one embodiment of an illumination subsystem configured to direct light to a wafer at multiple angles of incidence which may be included in any of the system embodiments described herein.

In one embodiment, the illumination subsystem is configured to direct the light to the wafer at multiple angles of incidence. FIG. 3 illustrates one embodiment of such an illumination subsystem, which may be included in any of the system embodiments described herein. As shown in FIG. 3, the illumination subsystem includes light source 60. Light source 60 may include any of the light sources described further herein. The illumination subsystem also includes beam splitter 62. Light from the light source is directed to the beam splitter, which separates the light into two different beams of light. The illumination subsystem also includes reflective optical elements 64 and 66. One of the beams of light produced by the beam splitter is directed to reflective optical element 64, and the other beam of light produced by the beam splitter is directed to reflective optical element 66. Reflective optical element 64 is configured to direct one beam of light to wafer 10 at an oblique angle of incidence. Reflective optical element 66 is configured to direct the other beam of light to wafer 10 at an oblique angle of incidence. The oblique angles of incidence at which the reflective optical elements direct light to the wafer are different. The oblique angles of incidence may be determined based on the characteristics of the wafer that are to be determined by the system. Reflective optical elements 64 and 66 may include any suitable reflective optical elements. The illumination subsystem shown in FIG. 3 may include any other suitable optical elements (not shown in FIG. 3) such as one or more polarizers and one or more refractive optical elements (e.g., configured to focus the light onto the wafer).

In one embodiment the first or second detection subsystem is configured to detect the light scattered from the wafer due to illumination at only a first of the multiple angles of incidence, and the third detection subsystem is configured to detect the light scattered from the wafer due to illumination at only a second of the multiple angles of incidence. For example, the first or second detection subsystem and the third detection subsystem may be configured in this manner based on the different characteristics (detection of which the detection subsystems may be configured (or optimized)), the angles of incidence at which the light is directed to the wafer, and the light scattering that will be produced by the different characteristics due to such illumination. In one such example, one surface spatial frequency band of surface roughness may scatter light strongly into one portion of the scattering hemisphere due to illumination at one of the angles of incidence, while a different surface spatial frequency band of surface roughness may scatter light strongly into a different portion of the scattering hemisphere due to illumination at a different angle of incidence. Therefore, the first or second detection subsystem and the third detection subsystem may be configured to collect light in the different portions of the scattering hemisphere to thereby detect (or detect optimally) the different surface spatial frequency bands of the surface roughness. Other characteristics of the first or second detection subsystem and the third detection subsystem may be determined in such a manner based on the multiple angles of incidence for detection (or optimal detection) of other characteristics described herein. In this manner, characteristics determined from haze properties such as roughness and haze defects of a surface can be determined using multiple angles of incidence for improved sensitivity and/or accuracy.

In one embodiment, the light directed to the wafer has multiple wavelengths. For example, as described further herein, a light source of the illumination subsystem may be configured to generate multiple wavelengths of light, and the illumination subsystem may be configured to direct at least some of the multiple wavelengths of light to the wafer.

In one embodiment, the first or second detection subsystem is configured to detect the light scattered from the wafer due to illumination with only a first of the multiple wavelengths, and the third detection subsystem is configured to detect the light scattered from the wafer due to illumination with only a second of the multiple wavelengths. For example, the first or second detection subsystem and the third detection subsystem may be configured in this manner based on the different characteristics (detection of which the first or second detection subsystem and the third detection subsystem may be configured or optimized), the multiple wavelengths of the light directed to the wafer, and the light scattering that will be produced by the different characteristics due to such illumination. In one such example, one surface spatial frequency band of surface roughness may scatter light strongly into one portion of the scattering hemisphere due to illumination at one of the wavelengths, while a different surface spatial frequency band of surface roughness may scatter light strongly into a different portion of the scattering hemisphere due to illumination at a different wavelength. Therefore, the first or second detection subsystem and the third detection subsystem may be configured to collect light in the different portions of the scattering hemisphere to thereby detect (or optimally detect) the different surface spatial frequency bands of the surface roughness. Other characteristics of the detection subsystems may be determined in such a manner based on the multiple wavelengths for detection (or optimal detection) of other characteristics described herein. In this manners characteristics determined from haze properties such as roughness and haze defects of a surface can be determined using multiple wavelengths of illumination.

The system may also include one or more additional detection subsystems or channels (not shown in FIG. 1), each of which may be configured (or optimized) for detection of another characteristic of the wafer. The one or more additional channels may be configured as described herein, for example, depending on the characteristic that each of the additional channels is to be used to detect and the characteristics that each of the additional channels is not to be used to detect. For example, the system may include an additional detection subsystem that may be configured (or optimized) to detect another spatially localized characteristic of the wafer and may not be configured (or optimized) to detect non-spatially localized characteristics of the wafer. In addition, or alternatively, the system may include an additional detection subsystem that may be configured (or optimized) to detect another non-spatially localized characteristic of the wafer and may not be configured (or optimized) to detect spatially localized characteristics of the wafer. For example, the system may include a fourth detection subsystem configured to detect light scattered from the wafer and to generate output responsive to the detected scattered light. The fourth detection subsystem may be configured (or optimized) for detection of a fourth characteristic and may not be configured (or optimized) for detection of the first, second, and third characteristics. The fourth characteristic may not be spatially localized in two dimensions and may include any such characteristics described herein. The fourth detection subsystem may be further configured (or optimized) for detection of the fourth characteristic and further not configured (or optimized) for detection of the first, second, and third characteristics as described further herein. The system shown in FIG. 1 may also include any number of such additional detection subsystems (e.g., a fourth and a fifth detection subsystem, etc.). The system shown in FIG. 1 may be further configured according to any other embodiment(s) described herein. In addition, the system shown in FIG. 1 may be further configured as described in U.S. Pat. No. 7,286,218 to Judell et al., which is incorporated by reference as if fully set forth herein.

Figure 4:
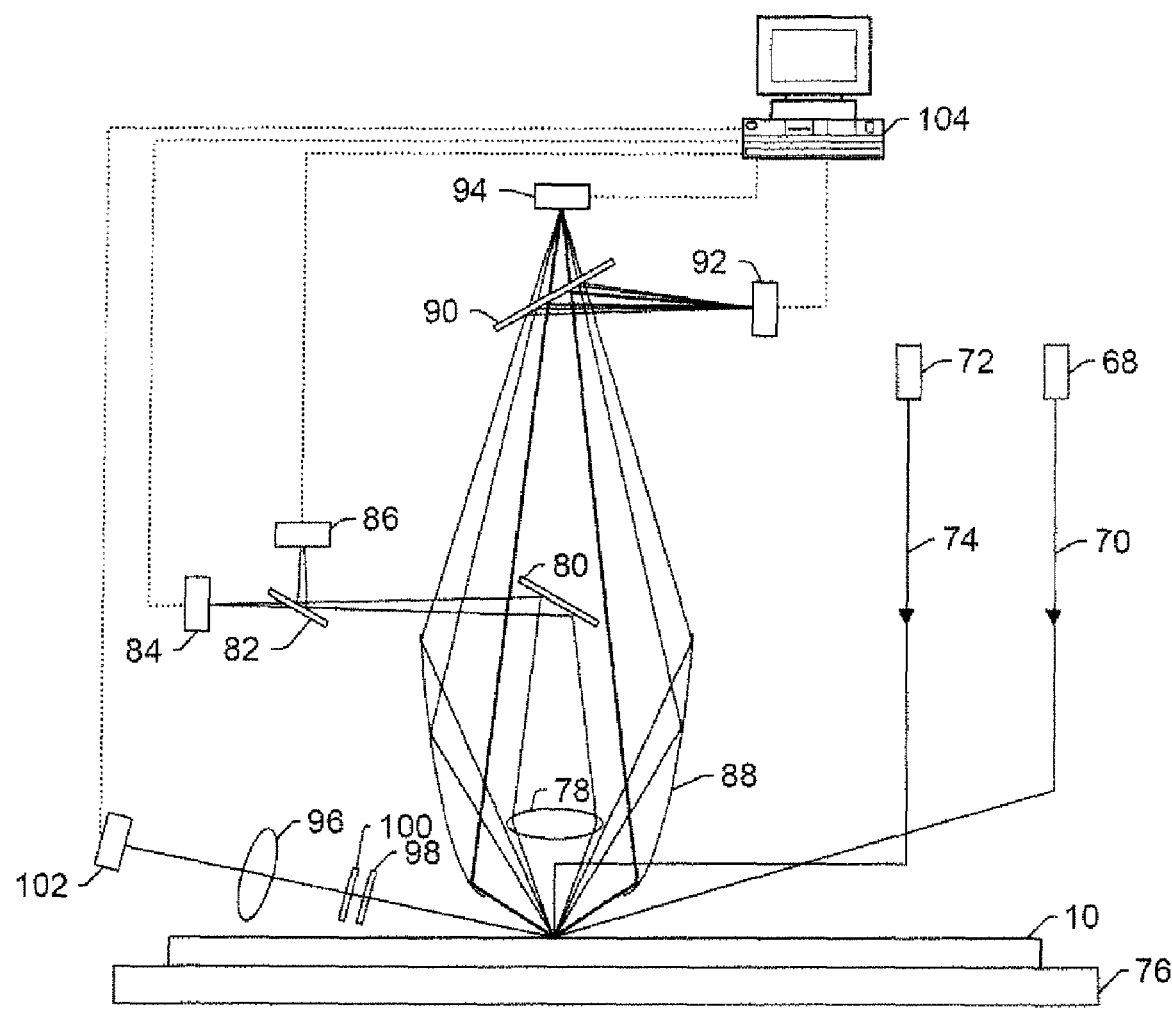
FIG. 4 is a schematic diagram illustrating a side view of another embodiment of a system configured to determine two or more characteristics of a wafer.

FIG. 4 illustrates another embodiment of a system configured to determine two or more characteristics of a wafer. The system includes an illumination subsystem configured to direct light to wafer 10. The illumination subsystem includes light source 68, which is configured to generate light 70. Light source 68 may include any of the light sources described herein and light 70 may include any of the light described herein. The illumination subsystem is configured to direct light 70 to wafer 10 at an oblique angle of incidence. The illumination subsystem may include a number of optical elements (not shown in FIG. 4) positioned in a path of light 70 such as folding mirror(s), beam splitter(s), polarizer(s), filter (s), and lenses. The oblique angle of incidence may vary depending on, for example, the characteristics of the light and the characteristics of the wafer. One suitable oblique angle of incidence may be about 70° from normal to the upper surface of the wafer.

The illumination subsystem also includes light source 72. Light source 72 is configured to generate light 74, which is directed by the illumination subsystem to wafer 10 at a substantially normal angle of incidence. Light source 72 may include any of the light sources described herein, and light 74 may include any of the light described herein. The illumination subsystem may include a number of optical components (not shown) positioned in the path of light 74. These optical components may include any of those described above. Therefore, the illumination subsystem is configured to direct light to the wafer at different angles of incidence. In addition, although the illumination subsystem is shown in FIG. 4 as configured to direct light to the wafer at an oblique angle of incidence and a substantially normal angle of incidence, the illumination subsystem may be configured to direct light to the wafer at two different oblique angles of incidence as described further herein.

Light sources 68 and 72 may include any suitable light sources such as lasers. In a different embodiment, the illumination subsystem may include a single light source (not shown) that is used to provide light for both oblique and normal illumination. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The illumination subsystem may include any other suitable combination of a single light source and beam multiplier(s) known in the art. In any of the above embodiments, light 70 may have one or more characteristics such as wavelength and/or polarization that are different than the characteristics of light 74. Alternatively, light 70 may have substantially the same characteristics as light 74.

Wafer 10 is supported on chuck 76, which may be rotated and translated such that light 70 and 74 illuminates an area or spot on the wafer that moves in a spiral path. For instance, in this system, a stage provides motion in the x direction. A spindle is mounted to the stage and provides rotation. The chuck is mounted on top of the spindle and supports the wafer. Alternatively, light 70 and 74 may be caused to move over the wafer in any manner known to those skilled in the art to trace the spiral path or another type of scan path across the wafer. Chuck 76 may be further configured as described herein.

Illumination of the wafer will cause scattering of the light from the wafer. In addition, both oblique incidence light and normal incidence light are scattered from the wafer. The system includes a first detection subsystem configured to detect light scattered from the wafer and to generate output responsive to the detected scattered light. The first detection subsystem includes lens collector 78, mirror 80, beam splitter 82, and detectors 84 and 86, which form a "narrow" channel of the first detection subsystem. In other words, light scattered from the illuminated area on the wafer along directions relatively close to normal to the surface of the wafer is collected and focused by lens collector 78. In this manner, lens collector 78 collects light scattered from the wafer at relatively "narrow" scattering angles. Lens collector 78 directs the collected light to mirror 80, which directs the light to beam splitter 82. Beam splitter 82 is configured to direct one portion of the light to detector 84 and the other portion of the light to detector 86. One detector may be used to detect light scattered at relatively narrow angles due to illumination by the normal incidence beam, and the other detector may be used to detect light scattered at relatively narrow angles due to illumination by the oblique incidence beam. Detectors 84 and 86 may include PMTs. In addition, detectors 84 and 86 may be similarly or differently configured. The narrow channel portion of the first detection subsystem may include any other suitable optical elements (not shown). For example, one or more polarizers, one or more apertures, one or more spectral filters, and the like may be placed in the path of the collected light. In addition, a spatial filter may be is included in the narrow channel portion of the first detection subsystem to prevent the specular reflection of the normal incidence beam from reaching detectors 84 and 86.

The first detection subsystem also includes ellipsoidal mirror 88, beam splitter 90, and detectors 92 and 94, which form a "wide channel" of the first detection subsystem. In other words, light scattered from the illuminated area on the wafer along directions relatively far from normal to the surface of the wafer is collected and focused by ellipsoidal mirror 88. In this manner, ellipsoidal mirror 88 collects light scattered from the wafer at relatively "wide" scattering angles. Ellipsoidal mirror 88 directs the collected light to beam splitter 90. Beam splitter 90 is configured to direct one portion of the light to detector 92 and the other portion of the light to detector 94. One detector may be used to detect light scattered at relatively wide angles due to illumination by the normal incidence beam, and the other detector may be used to detect light scattered at relatively wide angles due to the illumination by the oblique incidence beam. Detectors 92 and 94 may include PMTs. In addition, detectors 92 and 94 may be similarly or differently configured. The wide channel portion of the first detection subsystem may include any other suitable optical elements (not shown). For example, one or more polarizers, one or more apertures, one or more spectral filters, and the like may be placed in the path of the collected light.

In this manner, a single "detection subsystem" may be formed from multiple physical channels, either on the analog level or in post-processing. For example, as described above, the first detection subsystem of the system shown in FIG. 4 may include the narrow channel and the wide channel. The narrow and wide channels may form a single detection subsystem on the analog level or in post-processing in any suitable manner.

In one embodiment, the first detection subsystem is optimized for detection of only one of the first and second characteristics of the wafer and is not optimized for detection of the other of the first and second characteristics of the wafer. For example, the first detection subsystem may be configured (or optimized) for detection of a first characteristic of the wafer and may not be configured (of optimized) for detection of a second characteristic of the wafer. The first characteristic is spatially localized in at least one dimension, and the second characteristic is not spatially localized in two dimensions. The first characteristic may include any spatially localized characteristic described herein, and the second characteristic may include any non-spatially localized characteristic described herein. The first detection subsystem may be configured (or optimized) for detection of the first characteristic and not configured (or optimized) for detection of the second characteristics according to any of the embodiments described further herein.

The system also includes a second detection subsystem configured to detect light scattered from the wafer and to generate output responsive to the detected scattered light. The second detection subsystem includes collector 96, which is configured to collect light scattered from the wafer. Collector 96 may include a refractive optical element as shown in FIG. 4. Collector 96 may also be configured as described herein with respect to the collector of the second detection subsystem shown in FIG. 1. The second detection subsystem may also include polarizer 98 and aperture 100 positioned in the path of the light scattered from the wafer that is collected by collector 96. Polarizer 98 and aperture 100 may be configured as described herein. The second detection subsystem also includes detector 102. Detector 102 may be configured as described herein with respect to the detector of the second detection subsystem shown in FIG. 1. For example, detector 102 may be configured to detect the light scattered from the wafer, and in one embodiment the detector is not a PMT, which is advantageous as described further herein. The second detection subsystem may include any other components described herein (not shown in FIG. 4) such as an analog gain stage, an ADC, and digital processing.

In one embodiment, the second detection subsystem is optimized for detection of only one of the first and second characteristics of the wafer and is not optimized for detection of the other of the first and second characteristics of the wafer. For example, the second detection subsystem may be configured (or optimized) for detection of the second characteristic and may not be configured (or optimized) for detection of the first characteristic. The second detection subsystem shown in FIG. 4 may be configured (or optimized) for detection of only one of the first and second characteristics and may not be optimized for detection of the other of the first and second characteristics as described further herein. For example, in one embodiment, the second detection subsystem is configured (or optimized) for detection of only one of the first and second characteristics by configuration (or optimization) of a solid angle of the light scattered from the wafer that is collected and detected by the second detection subsystem, a polarization of the light scattered from the wafer that is collected and detected by the second detection subsystem, a wavelength of the light scattered from the wafer that is collected and detected by the second detection subsystem, a detector of the second detection subsystem, an analog gain stage of the second detection subsystem, an ADC of the second detection subsystem, and digital processing performed by the second detection subsystem.

The first and second detection subsystems of the system shown in FIG. 4 may be further configured as described herein. For example, in one embodiment, the first or second detection subsystem is configured such that a substantial portion of the light scattered from the wafer that is detected by the first or second detection subsystem includes light due to wafer scattering or haze. Such an embodiment of the first or second detection subsystem may be configured as described further herein. In another embodiment, a resolution of the first detection subsystem is optimized for detection of only one of the first and second characteristics and is not optimized for detection of the other of the first and second characteristics, and a resolution of the second detection subsystem is optimized for detection of the other of the first and second characteristics and is not optimized for detection of the one of the first and second characteristics.

In one embodiment, solid angles of the light scattered from the wafer that is collected and detected by the first and second detection subsystems are different. For example, a solid angle of the light scattered from the wafer that is collected and detected by the second detection subsystem may be smaller than a solid angle of the light scattered from the wafer that is collected and detected by the first detection subsystem. In one such example, as shown in FIG. 4, the first detection subsystem may collect and detect light over a substantially larger solid angle than the second detection subsystem. In one embodiment, a solid angle of the light scattered from the wafer that is collected and detected by the second detection subsystem is mutually exclusive from a solid angle of the light scattered from the wafer that is collected and detected by the first detection subsystem. For example, as shown in FIG. 4, the solid angles of the scattered light that are collected and detected by the different detection subsystems may be mutually exclusive. The solid angles of the scattered light that are collected and detected by the different detection subsystems of the system shown in FIG. 4 may be mutually exclusive as described further herein.

In one embodiment, the first detection subsystem includes a first collector configured to collect the light scattered from the wafer, and the second detection subsystem includes a second collector configured to collect the light scattered from the wafer. In this manner, the first and second detection subsystems may include different collectors. For example, as shown in FIG. 4, the first detection subsystem includes collectors 78 and 88, and the second detection subsystem includes collector 96. The first and second collectors may be further configured as described herein.

In one embodiment, the maximum value of the output that can be generated and processed by the second detection subsystem is matched to the maximum value of the scattered light that would be produced by the second characteristic. The maximum value of the output that can be generated and processed by the second detection subsystem may be matched to the maximum value of the scattered light that would be produced by the second characteristic as described further herein.

In one embodiment, the first and second detection subsystems are configured to simultaneously detect the light scattered from the wafer. For example, as shown in FIG. 4, when the wafer is being illuminated with light 70 and/or light 74, both of the detection subsystems may collect and detect light scattered from the wafer. In this manner, like the system shown in FIG. 1, the system shown in FIG. 4 can determine two or more characteristics of the wafer simultaneously.

The system also includes a computer subsystem configured to determine a first characteristic of the wafer using only the output generated by one of the first and second detection subsystems and to determine a second characteristic of the wafer using only the output generated by the other of the first and second detection subsystems. For example, as shown in FIG. 4, the system includes computer subsystem 104 coupled to detectors 84, 86, 92, 94, and 102 by transmission media as shown by the dotted lines in FIG. 4. The transmission media may include any suitable transmission media known in the art. In addition, one or more additional components (not shown) may be interposed between the detectors and the computer subsystem such as analog gain stages, ADCs, and digital processing, which may be configured as described herein. In this manner, output generated by the detection subsystems can be sent to the computer subsystem. The computer subsystem may be configured to use only the output generated by one of the first and second detection subsystems to determine the first characteristic as described herein. In addition, the computer subsystem may be configured to use only the output generated by the other of the first and second detection subsystems to determine the second characteristic as described herein. The computer subsystem may also be further configured as described herein.

The system shown in FIG. 4 may be further configured according to any other embodiment(s) described herein. For example, the system embodiment shown in FIG. 4 may include a third detection subsystem, a fourth detection subsystem, etc. configured as described herein.

The system shown in FIG. 4 may also be further configured as described in commonly owned U.S. Pat. No. 6,201,601 to Vaez-Iravani et al. and U.S. Pat. No. 6,538,730 to Vaez-Iravani et al., which are incorporated by reference as if fully set forth herein. For example, two or more of the multiple detection subsystems included in the system shown in FIG. 4 may include a common collector (e.g., the ellipsoidal collector) that is segmented in collection or detection space as described in these patents such that the different detection subsystems detect light scattered across different portions of the collection space of the common collector. In one such example, the numerical aperture (NA) of the ellipsoidal collector may be segmented (e.g., using a reflective optical element) such that light collected across a first portion of the NA is directed to a first detector while light collected across a second portion of the NA is directed to a second detector. Therefore, one detection subsystem may include a collector and a first detector, and another detection subsystem may include the same collector and a second detector. In another example, the scattered light that is collected by the ellipsoidal collector may be directed to an array of optical elements such as optical fibers configured to separately transmit the light to different detectors. In this manner, one detection subsystem may include a collector, a portion of the optical fibers, and a portion of the detectors, and another detection subsystem may include the collector, a different portion of the optical fibers, and a different portion of the detectors. In an additional example, the scattered light that is collected by the ellipsoidal collector may be directed to a segmented detector such as a multi-anode PMT configured such that different portions of the segmented detector detect light scattered into different solid angles. As such, one detection subsystem may include a collector and a portion of the segmented detector, and another detection subsystem may include the same collector and a different portion of the same segmented detector. One or more characteristics of each of the detection subsystems described in the above examples may be further configured as described herein to configured (or optimize) the detection subsystems for detection of a spatially localized characteristic of the wafer or a non-spatially localized characteristic of the wafer.

It is noted that FIGS. 1 and 4 are provided herein to generally illustrate different configurations for the system embodiments described herein. Obviously, the system configurations described herein may be altered to optimize the performance of the system as is normally performed when designing a commercial system. In addition, the systems described herein may be implemented using an existing inspection system (e.g. by modifying an existing inspection system based on the embodiments described herein) such as the SPx series of tools, which are commercially available from KLA-Tencor, San Jose, Calif. For some such systems, the functionality of the system embodiments described herein may be provided as optional functionality of the system (e.g., in addition to other functionality of the system). In this manner, the embodiments described herein may be used to provide detection (or optimal detection) of each of multiple characteristics of a wafer in the SPx family of products. Alternatively, the systems described herein may be designed "from scratch" to provide completely new systems.

In some embodiments, the systems described herein may be configured as a "stand alone tool" or a tool that is not physically coupled to a process tool. However, such a system may be coupled to the process tool by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a "cluster tool," or a number of process modules coupled by a common handler.

As described above, the detection subsystems may be configured (or optimized) for detection of different characteristics of a wafer (e.g., defects and surface characteristics). However, the different detection subsystems do not have to be explicitly configured (or optimized) for detection of different characteristics of a wafer. For example, one can use uniform criteria (e.g., surface noise and maximum signal) across the detection subsystems to select one or more characteristics of the detection subsystems. In addition, one can use subsystem-dependent criteria to select one or more characteristics of the detection subsystems and just use the output produced by such detection subsystems. In addition, the first and second detection subsystems do not have to be assigned for detection of different characteristics of the wafer up-front (e.g., dedicate channel X to a surface characteristic, channel Y to defects, etc.). For example, the detection of different characteristics can be assigned to different detection subsystems in post-processing, after analyzing statistical behavior of the data.

An additional embodiment relates to a method for determining two or more characteristics of a wafer. The two or more characteristics may include any of the characteristics described herein. The method includes directing light to the wafer using an illumination subsystem. Directing the light to the wafer may be performed as described further herein. The illumination subsystem may be configured as described further herein.

The method also includes detecting light scattered from the wafer and generating output responsive to the detected scattered light using a first detection subsystem of a system. Detecting the scattered light and generating the output using the first detection subsystem may be performed as described further herein. The first detection subsystem and the system may be configured as described herein.

The method also includes detecting light scattered from the wafer and generating output responsive to the detected scattered light using a second detection subsystem of the system. Detecting the scattered light and generating the output using the second detection subsystem may be performed as described further herein. The second detection subsystem may be configured as described herein.

The method also includes determining a first characteristic of the wafer using only the output generated by one of the first and second detection subsystems. Determining the first characteristic may be performed as described further herein. The first characteristic is spatially localized in at least one dimension. The first characteristic may include any such characteristic described herein. In addition, the method includes determining a second characteristic of the wafer using only the output generated by the other of the first and second detection subsystems. Determining the second characteristic may be performed as described further herein. The second characteristic is not spatially localized in two dimensions.

Each of the embodiments of the method described above may include any other step(s) described herein. For example, each of the embodiments of the method described above may include any of the step(s) that can be performed by any of the system(s) described herein. In addition, each of the embodiments of the method described above may be performed by any of the system embodiments described herein and shown in FIGS. 1 and 4.

Figure 5:
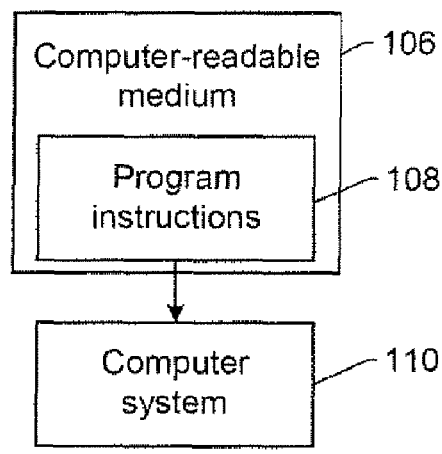
FIG. 5 is a block diagram illustrating one embodiment of a computer-readable medium that includes program instructions executable on a computer system for performing a computer-implemented method for determining two or more characteristics of a wafer.

Another embodiment relates to a computer-readable medium that includes program instructions executable on a computer system for performing a computer-implemented method for determining two or more characteristics of a wafer. One such embodiment is shown in FIG. 5. For example, as shown in FIG. 5, computer-readable medium 106 includes program instructions 108 executable on computer system 110 for performing a computer-implemented method for determining two or more characteristics of a wafer.

The computer-implemented method includes determining a first characteristic of the wafer using only output generated by detecting light scattered from the wafer using one of first and second detection subsystems of a system. Determining the first characteristic of the wafer may be performed as described further herein. The first and second detection subsystems and the system may be configured as described herein. The first characteristic is spatially localized in at least one dimension. The first characteristic may include any such characteristic described herein.

The computer-implemented method also includes determining a second characteristic of the wafer using only output generated by detecting light scattered from the wafer using the other of the first and second detection subsystems. Determining the second characteristic of the wafer may be performed as described further herein. The second characteristic is not spatially localized in two dimensions. The second characteristic may include any such characteristic described herein.

The computer-implemented method for which the program instructions are executable may include any other step(s) of any other method(s) described herein.

Program instructions 108 implementing methods such as those described herein may be transmitted over or stored on computer-readable medium 106. The computer-readable medium may be a transmission medium such as a wire, cable, or wireless transmission link. The computer-readable medium may also be a storage medium such as a read-only memory, a RAM, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 110 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

The computer system described above may be configured as a stand-alone system that does not form part of an inspection, metrology, review, or other tool. In such an embodiment, the computer system may be configured to receive and/or acquire data or information from other systems (e.g., output generated by the detection subsystems included in a system described herein) by a transmission medium that may include "wired" and/or "wireless" portions. In this manner, the transmission medium may serve as a data link between the computer system and the other system. In addition, the computer system may send data to the other system via the transmission medium. Such data may include any of the results of the methods described herein. In other embodiments, however, the computer system is included in an inspection system. The inspection system may be configured as described herein.

The characteristics determined by the embodiments described herein may be used to alter a parameter of a process or a process tool using a feedback control technique, a feedforward control technique, or an in situ control technique. The parameter of the process or the process tool may be altered automatically.

The embodiments described herein may also include or be configured for storing results of one or more steps of one or more methods or computer-implemented methods described herein in a storage medium. The results may include any of the results described herein. The results may be stored in any manner known in the art. The storage medium may include any suitable storage medium known in the art. After the results have been stored, the results can be accessed in the storage medium and used by any of the method or system embodiments described herein, any other method, or any other system. Furthermore, the results may be stored "permanently," "semi-permanently," temporarily, or for some period of time. For example, the storage medium may be random access memory (RAM), and the results may not necessarily persist indefinitely in the storage medium.

Further modifications and alternative embodiments of various aspects of the invention may be apparent to those skilled in the art in view of this description. For example, systems and methods for determining two or more characteristics of a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to determine two or more characteristics of a wafer, comprising:
    an illumination subsystem configured to direct light to the wafer;
    a first detection subsystem configured to detect light scattered from the wafer and to generate output responsive to the detected scattered light;
    a second detection subsystem configured to detect light scattered from the wafer and to generate output responsive to the detected scattered light; and
    a computer subsystem configured to determine a first characteristic of the wafer using only the output generated by one of the first and second detection subsystems and to determine a second characteristic of the wafer using only the output generated by the other of the first and second detection subsystems, wherein the first characteristic is spatially localized in at least one dimension, and wherein the second characteristic is not spatially localized in two dimensions.

2. The system of claim 1, wherein the first detection subsystem is optimized for detection of only one of the first and second characteristics of the wafer and is not optimized for detection of the other of the first and second characteristics of the wafer.

3. The system of claim 1, wherein the second detection subsystem is optimized for detection of only one of the first and second characteristics of the wafer and is not optimized for detection of the other of the first and second characteristics of the wafer.

4. The system of claim 1, wherein the first detection subsystem is optimized for detection of only one of the first and second characteristics of the wafer and is not optimized for detection of the other of the first and second characteristics of the wafer, and wherein the second detection subsystem is optimized for detection of only the other of the first and second characteristics of the wafer and is not optimized for detection of the one of the first and second characteristics of the wafer.

5. The system of claim 1, wherein the first characteristic is spatially localized in at least one dimension in that a lateral scale of the first characteristic in at least one dimension is smaller than a point spread function of the system.

6. The system of claim 1, wherein the first characteristic comprises defects on a surface of the wafer, and wherein the defects are spatially localized in one or two dimensions.

7. The system of claim 1, wherein the second characteristic is not spatially localized in two dimensions in that lateral scales of the second characteristic in two dimensions are larger than a point spread function of the system.

8. The system of claim 1, wherein the first or second detection subsystem is further configured such that a substantial portion of the light scattered from the wafer that is detected by the first or second detection subsystem comprises light due to wafer surface scattering or haze.

9. The system of claim 1, wherein the second characteristic comprises surface roughness, film thickness, film composition, material crystallinity, surface optical constants, nanofeature characteristics, pattern linewidths, or process parameters.

10. The system of claim 1, wherein the second characteristic comprises surface roughness variations over only a subset of all surface spatial frequency bands of the surface roughness.

11. The system of claim 1, wherein the first and second detection subsystems are further configured to simultaneously detect the light scattered from the wafer.

12. The system of claim 1, wherein the first detection subsystem comprises a first collector configured to collect the light scattered from the wafer, and wherein the second detection subsystem comprises a second collector configured to collect the light scattered from the wafer.

13. The system of claim 1, wherein solid angles of the light scattered from the wafer that is collected and detected by the first and second detection subsystems are different.

14. The system of claim 1, wherein a solid angle of the light scattered from the wafer that is collected and detected by the second detection subsystem is mutually exclusive from a solid angle of the light scattered from the wafer that is collected and detected by the first detection subsystem.

15. The system of claim 1, wherein the second detection subsystem is optimized for detection of only one of the first and second characteristics by optimization of a solid angle of the light scattered from the wafer that is collected and detected by the second detection subsystem, a polarization of the light scattered from the wafer that is collected and detected by the second detection subsystem, a wavelength of the light scattered from the wafer that is collected and detected by the second detection subsystem, a detector of the second detection subsystem, an analog gain stage of the second detection subsystem, an analog-to-digital converter of the second detection subsystem, and digital processing performed by the second detection subsystem.

16. The system of claim 1, wherein the maximum value of the output that can be generated and processed by the second detection subsystem is matched to the maximum value of the scattered light that would be produced by the second characteristic.

17. The system of claim 1, wherein the second detection subsystem comprises a detector configured to detect the light scattered from the wafer, and wherein the detector is not a photomultiplier tube.

18. The system of claim 1, wherein a resolution of the first detection subsystem is optimized for detection of only one of the first and second characteristics and is not optimized for detection of the other of the first and second characteristics, and wherein a resolution of the second detection subsystem is optimized for detection of the other of the first and second characteristics and is not optimized for detection of the one of the first and second characteristics.

19. The system of claim 1, further comprising a third detection subsystem configured to detect light scattered from the wafer and to generate output responsive to the detected scattered light, wherein the computer subsystem is further configured to determine a third characteristic of the wafer using only the output generated by the third detection subsystem, and wherein the third characteristic is not spatially localized in two dimensions.

20. The system of claim 19, wherein the computer subsystem is further configured to determine one or more properties of a film formed on the wafer using the output generated by the first or second detection subsystem in combination with the output generated by the third detection subsystem.

21. The system of claim 19, wherein the illumination subsystem is further configured to direct the light to the wafer at multiple angles of incidence, wherein the first or second detection subsystem is further configured to detect the light scattered from the wafer due to illumination at only a first of the multiple angles of incidence, and wherein the third detection subsystem is further configured to detect the light scattered from the wafer due to illumination at only a second of the multiple angles of incidence.

22. The system of claim 19, wherein the light directed to the wafer has multiple wavelengths, wherein the first or second detection subsystem is further configured to detect the light scattered from the wafer due to illumination with only a first of the multiple wavelengths, and wherein the third detection subsystem is further configured to detect the light scattered from the wafer due to illumination with only a second of the multiple wavelengths.

23. The system of claim 19, wherein the second characteristic comprises surface roughness variations over one or more first surface spatial frequency bands of the surface roughness, and wherein the third characteristic comprises surface roughness variations over one or more second surface spatial frequency bands of the surface roughness.

24. A method for determining two or more characteristics of a wafer, comprising:

directing light to the wafer using an illumination subsystem;

detecting light scattered from the wafer and generating output responsive to the detected scattered light using a first detection subsystem of a system;

detecting light scattered from the wafer and generating output responsive to the detected scattered light using a second detection subsystem of the system;

determining a first characteristic of the wafer using only the output generated by one of the first and second detection subsystems, wherein the first characteristic is spatially localized in at least one dimension; and determining a second characteristic of the wafer using only the output generated by the other of the first and second detection subsystems, wherein the second characteristic is not spatially localized in two dimensions.

25. A non-transitory computer-readable medium containing computer program instructions stored therein, wherein the program instructions are executable on a computer system for performing a computer-implemented method for determining two or more characteristics of a wafer, and wherein the computer-implemented method comprises:

determining a first characteristic of the wafer using only output generated by detecting light scattered from the wafer using one of first and second detection subsystems of a system, wherein the first characteristic is spatially localized in at least one dimension; and determining a second characteristic of the wafer using only output generated by detecting light scattered from the wafer using the other of the first and second detection subsystems, wherein the second characteristic is not spatially localized in two dimensions.

* * * * *